United States Patent
Hauck et al.

[11] B 3,984,419
[45] Oct. 5, 1976

[54] PERHYDROFLUORENETETROL AND PERHYDRO-PHENANTHRENETETROL DERIVATIVES

[75] Inventors: Frederic Peter Hauck, Somerville; Christopher Michael Cimarusti, Somerset, both of N.J.

[73] Assignee: E. R. Squibb & Sons, Inc., Princeton, N.J.

[22] Filed: Feb. 28, 1974

[21] Appl. No.: 447,000

[44] Published under the second Trial Voluntary Protest Program on February 3, 1976 as document No. B 447,000.

Related U.S. Application Data

[63] Continuation of Ser. No. 265,065, June 21, 1972, abandoned.

[52] U.S. Cl. .................. 260/293.56; 260/243 B; 260/247.2 B; 260/247.5 R; 260/268 TR; 260/293.62; 260/326.33; 260/326.5 C; 260/343.3 R; 260/475 SC; 260/488 R; 260/505 R; 260/558 R; 260/561 R; 260/563 P; 260/247.7 Z; 260/570.5 CA; 260/618 F; 260/247.7 V; 424/246; 424/248; 424/250; 424/267; 424/274; 424/311; 424/325

[51] Int. Cl.$^2$ ............... C07D 295/08; C07D 295/10

[58] Field of Search .............. 260/293.56, 326.5 C, 260/326.33, 488 B, 563 R, 563 P, 243 B, 247.2 B, 247.5 R, 247.7 F, 268 TR

[56] References Cited
UNITED STATES PATENTS
3,751,420   8/1973   Hauck et al. ............... 260/293.58

*Primary Examiner*—G. Thomas Todd
*Attorney, Agent, or Firm*—Lawrence S. Levinson; Merle J. Smith; Donald J. Barrack

[57] ABSTRACT

Compounds are provided having the structure

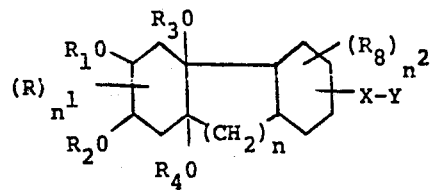

wherein $n$ is 1 or 2, $n^1$ is 0, 1 or 2 and $n^2$ is 0, 1, 2 or 3, $R_1$, $R_2$, $R_3$ and $R_4$ may be the same or different and can be hydrogen, lower alkyl, halolower alkyl, acyl, lower alkoxy-carbonyl

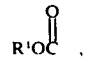

amido

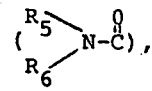

or lower alkoxyalkylene, R can be lower alkoxy, lower alkyl or cycloalkyl, $R_8$ can be hydrogen, lower alkyl, cycloalkyl, hydroxy, dialkylaminoalkyl or $R_9O(CH_2)q$—. X is a single bond or a straight or branched bivalent aliphatic radical and Y is

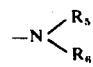

These compounds are useful in the treatment of hypertension.

18 Claims, No Drawings

PERHYDROFLUORENETETROL AND PERHYDRO-PHENANTHRENETETROL DERIVATIVES

This is a continuation of application Ser. No. 265,065, filed June 21, 1972, and now abandoned.

COMPOUNDS OF THE INVENTION

The present invention relates to perhydrofluorene and perhydrophenanthrene derivatives which have a lowering effect on blood pressure and are useful in the treatment of hypertension, in mammallian species, for example, rats and dogs. In addition, the compounds of the invention can be employed as antibiotics. A compound of formula I (below) as well as its physiologically acceptable acid salts may be compounded according to pharmaceutical practice in oral or parenteral dosage forms such as tablets, capsules, elixirs, injectables or powders for administration of about 100 mg. to 400 mg. per day, preferably 125 mg. to 175 mg. per day, in 2 to 4 divided doses.

Furthermore, the compounds of this invention are useful as water softeners.

The compounds of the invention have the general formula

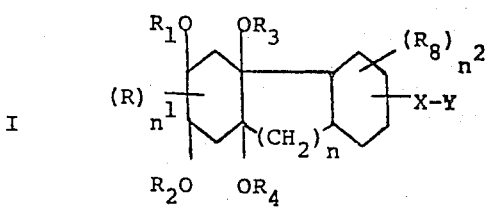

I wherein n is 1 or 2, $n^1$ is 0, 1 or 2 and $n^2$ is 0, 1, 2 or 3, $R_1$, $R_2$, $R_3$ and $R_4$ may be the same or different and represent hydrogen, acyl, lower alkyl, halolower alkyl, lower alkoxy-carbonyl

wherein $R^1$ is alkyl, amido

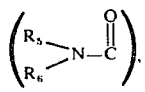

or lower alkoxyalkylene, R can be lower alkoxy, lower alkyl or cycloalkyl, $R_8$ can be hydrogen, lower alkyl, cycloalkyl, hydroxy, dialkylaminoalkyl or $R_9O(CH_2)q$. Where $n^1$ and $n^2$ are more than 1, the R radicals can be the same or different and the $R_8$ radicals can be the same or different. X is a single bond or a straight or branched chain bivalent aliphatic radical, and Y is

wherein $R_5$ and $R_6$ may be the same or different and are selected from the group consisting of hydrogen, lower alkyl, lower alkoxy, halo-lower alkyl, monocyclic cycloalkyl, monocyclic cycloalkyl-lower alkyl, lower alkanoyl, halo-lower alkanoyl, hydroxy-lower alkyl, monocyclic aryloyl, monocyclic aryl, monocyclic aryl-lower alkyl, monocyclic heterocyclic, monocyclic heterocyclic alkyl or N,N-dialkyl sulfamoyl.

Where $R_8$ is $R_9O(CH_2)_q$, $R_9$ can be any of the $R_1$ to $R_4$ groups mentioned above. Thus, where $R_1$, $R_2$, $R_3$ and $R_4$ are hydrogen, $R_9$ will be hydrogen. Where one or more of $R_1$ to $R_4$ is acyl or any of the other $R_1$ to $R_4$ groups mentioned above, $R_9$ will correspond to the acyl group or any of the other $R_1$ to $R_4$ groups, respectively.

The $(CH_2)_q$ portion is an alkylene group wherein q is 1 to 10, and is defined in a manner similar to $(CH_2)_p$ below.

The

group may also form a heterocyclic radical.

X represents straight or branched chain bivalent aliphatic hydrocarbon groups having from zero to about ten carbon atoms, such as a straight or branched alkylene group of the structure $(CH_2)_p$ where P is zero to ten, such as methylene, ethylene, propylene, trimethylene, butylene, dimethylethylene, isopropylene, isobutylene and the like. Furthermore, X can correspond to any of the lower alkyl groups exemplified hereinafter; $R_1$ $R_2$, $R_3$ and/or $R_4$ and $R_5$ and/or $R_6$ may be an acyl radical of a hydrocarbon carboxylic acid of less than twelve carbon atoms, which may be exemplified by the lower alkanoic acids (e.g., formic, acetic, propionic, butyric, valeric, trimethyl acetic and caproic acids), the lower alkenoic acids (e.g., acrylic, methacrylic, crotonic, 3-butenoic and senecioic acids), the monocyclic aryl-carboxylic acids (e.g., benzoic and toluic acids), the monocyclic aryl-lower alkanoic acids [e.g., phenacetic, β-phenylpropionic, α-phenylbutyric, and 5-(p-methylphenyl)pentanoic acids], the cycloalkyl carboxylic acids (e.g., cyclobutane carboxylic acid, cyclopentane carboxylic acid and cyclohexane carboxylic acid), the cycloalkenyl carboxylic acids (e.g., 2-cyclobutene carboxylic acid and 3-cyclopentene carboxylic acid), the cycloalkyl and cycloalkenyl-lower alkanoic acids [e.g., cyclohexaneacetic, α-cyclopentanebutyric, 2-cyclopenteneacetic and 3-(3-cyclohexene) pentenoic acids], and the like.

The alkanoic acids may include halogen substituents, for example, trifluoroacetic acid. In addition, other acyl groups which can be employed are angeloyl, veratroyl, vanilloyl, erythro-2-hydroxy-2-methyl-3-acetoxybutyryl, (1)-2-methylbutyryl, (d)-2-hydroxy-2-methylbutyryl, (d)-threo-2,3-dihydroxy-2-methylbutyryl and (1)-erythro-2,3-dihydroxy-2-methylbutyryl.

The term "lower alkyl" as employed herein includes both straight and branched chain radicals of up to eight carbon atoms, for instance, methyl, ethyl, propyl, isopropyl butyl, t-butyl, isobutyl, pentyl, hexyl, isohexyl, heptyl, 4,4-dimethylpentyl, octyl, 2,2,4-trimethylpentyl, and the like. With respect to $R^8$, lower alkyl can include a dialkylamino substituent to form a dialkylaminoalkyl group. Examples of such groups include dimethylaminomethyl, ethylmethylaminopropyl and diethylaminoethyl.

Alkyl radicals substituted by F, Br, Cl or I are encompassed by the term halo-lower alkyl. Trifluoromethyl is a preferred halo-lower alkyl radical.

The term "lower alkoxy" includes straight and branched chain radicals which correspond to the above lower alkyl groups attached to an oxygen atom.

The term "monocyclic aryl" as employed herein contemplates monocyclic carbocyclic aryl radicals, for instance, phenyl and substituted phenyl radicals, such as lower alkyl phenyl (e.g., o, m- or p-tolyl, ethylphenyl, butylphenyl, and the like), di(lower alkyl)phenyl (e.g., 2,4-dimethylphenyl, 3,5-diethylphenyl, and the like), halophenyl (e.g., chlorophenyl, bromophenyl, iodophenyl, fluorophenyl), o-, m- or p-nitrophenyl dinitrophenyl, (e.g., 3,5-dinitrophenyl, 2,6-dinitrophenyl, and the like), trinitrophenyl (e.g., picryl) and mono-, di- or trialkoxyphenyl, such as mono-, di- or tri-methoxyphenyl.

The term "monocyclic aryoyl" includes any of the above aryl groups linked to a carbonyl group.

The term "monocyclic cycloalkyl" and "monocyclic cycloalkenyl" includes cyclic radicals containing from 3 to 6 ring members (e.g., cyclopropyl, cyclobutyl, cyclopentyl, cyclohexyl, cyclobutenyl and cyclohexenyl).

As indicated hereinbefore,

may form a heterocyclic radical. The symbols $R_5$ and $R_6$ may together represent the carbon (and hydrogen) and the oxygen, sulfur or nitrogen atoms which, with the nitrogen or carbon atoms in the above group, form a 5-, 6- or 7-membered nitrogen heterocyclic containing not more than one hetero atom in addition to the nitrogen already shown in the group and less than 21 atoms in the radical (excluding hydrogen). The heterocyclic radicals may include one to three substituents including lower alkoxy or lower alkyl as defined hereinafter; trihalomethoxy, such as trifluoromethoxy; trihalomethylmercapto, such as trifluoromethylmercapto; N,N-dialkylsulfamoyl groups, such as N,N-dimethylsulfamoyl; lower alkanoyl groups as defined hereinafter such as acetyl, propionyl, and the like; hydroxy; hydroxy-lower alkyl, such as hydroxymethyl, 2-hydroxyethyl, or the like; hydroxy-lower alkoxy-lower alkyl, such as 2-(2-hydroxyethoxy)ethyl, or the like; alkanoyloxy containing an alkanoyl as defined herein; alkanoyloxy-lower alkyl (up to about 14 carbons in the alkanoyl group), such as 2-heptanoyloxyethyl; carbo-lower alkoxy, such as carbomethoxy, carboethoxy, carbopropoxy, or the like; or 2-(alkanoyloxy-lower alkoxy) lower alkyl (with up to about 14 carbons in the alkanoyl group), such as 2-(decanoyloxyethoxy)-ethyl, or the like.

Illustrative of the heterocyclic radicals represented by $R_5$, $R_6$, or

are the following: piperidino; (lower alkyl)piperidino [e.g., 2-, 3-, or 4-(lower alkyl)-piperidino or 4(N-lower alkyl)piperidino such as 2-(ethyl)-piperidino or 4-(N-isopropyl)-piperidino]; di(lower alkyl)piperidino [e.g., 2,4-, 2,5- or 3,5-di(lower alkyl)piperidino such as 2,4-dimethylpiperidino or 2,5-di-t-butyl piperidino]; 2-, 3- or 4-hydroxymethyl piperidino; (lower alkoxy)-piperidino [e.g., 2-methoxypiperidino or 3-methoxypiperidino]; hydroxypiperidino [e.g., 3-hydroxy- or 4-hydroxypiperidino]; aminomethylpiperidino [e.g., 4-aminomethylpiperidino]; pyrrolidino; (lower alkyl)-pyrrolidino [e.g., 3-methyl-pyrrolidino]; di(loweralkyl)pyrrolidino [e.g., 3,4-dimethyl-pyrrolidino]; 2- or 3-hydroxypyrrolidino; (lower alkoxy)pyrrolidino [e.g., 2-methoxypyrrolidino]; morpholino; (lower alkyl)morpholino [e.g., 3-methylmorpholino]; di(lower alkyl)-morpholino [e.g., 3,5-dimethylmorpholino]; (lower alkoxy)morpholino [e.g. 2-methoxymorpholino]; thiamorpholino; (lower alkyl)thiamorpholino [e.g., 3-methylthiamorpholino]; di(lower alkyl)thiamorpholino [e.g., 3,5-dimethylthiamorpholino]; (lower alkoxy) thiamorpholino [e.g., 3-methoxythiamorpholino]; piperazino; (lower alkyl)piperazino [e.g., $N^4$-methylpiperazino]; di(lower alkyl)-piperazino [e.g., 2,5-dimethylpiperazino or 2,6-dimethylpiperazino]; (lower alkoxy)piperazino [e.g., 2-methoxypiperazino]; (hydroxy-lower alkyl)piperazino [e.g., $N^4$-(2-hydroxyethyl)piperazino]; (alkanoyloxy-lower alkyl)piperazino wherein the alkanoyloxy group has up to 14 carbons [e.g., $N^4$-(2-heptanoyloxyethyl)piperazino or $N^4$-(2-dodecanoyloxyethyl)-piperazino]; (hydroxy-lower alkoxy-lower alkyl)piperazino [e.g., (hydroxy-methoxymethyl)piperazino]; (carbo-lower alkoxy)piperazino [e.g., $N^4$-(carbomethoxy-, carboethoxy-, or carbopropoxy)piperazino]; homopiperazino; or $N^4$-(hydroxylower alkyl)homopiperazino [e.g., $N^4$-(2-hydroxyethyl)homopiperazino]; piperidyl; (lower alkyl)-piperidyl [e.g., 1-, 2-, 3- or 4-(lower alkyl)piperidyl, such as 1-N-methylpiperidyl or 3-ethylpiperidyl]; di(-lower alkyl)piperidyl [e.g., 2,4-, 2,5-, or 3,5-di(lower alkyl)piperidyl wherein lower alkyl is methyl, ethyl, n-propyl, isopropyl, etc.]; lower alkoxy piperidyl [e.g., 3-methoxypiperidyl or 2-ethoxypiperidyl]; hydroxy piperidyl [e.g., 3-hydroxy- or 4-hydroxypiperidyl]; aminomethylpiperidyl [e.g., 4-aminoethylpiperidyl]; pyrrolidyl; lower alkyl pyrrolidyl [e.g., 1-N-methylpyrrolidyl]; di(lower alkyl)pyrrolidyl [e.g., 2,3-dimethylpyrrolidyl]; lower alkoxy pyrrolidyl [e.g., 4-N-methoxypyrrolidyl]; morpholinyl; (lower alkyl)morpholinyl [e.g., 3-methylmorpholinyl]; di(lower alkyl)morpholinyl [e.g., 3-methyl-4-N-ethylmorpholinyl]; (lower alkoxy)morpholinyl [e.g., 2-ethoxymorpholinyl]; thiamorpholinyl; (lower alkyl)thiamorpholinyl [e.g., 3-ethylthiamorpholinyl]; di(lower alkyl)thiamorpholinyl [e.g., 3-methyl-4-N-ethylthiamorpholinyl]; lower alkoxy thiamorpholino [e.g., 3-methoxythiamorpholinyl]; piperazinyl; alkyl, dialkyl, alkoxy or hydroxy-lower alkyl substituted piperazinyl.

The N-oxides of the compounds of formula I where Y represents a nitrogen containing heterocyclic radical can be formed by reacting such formula I compounds with a peracid such as m-chloroperoxy benzoic acid, perbenzoic acid or monoperphthalic acid in a suitable solvent such as chloroform.

The compounds of formula I form acid addition salts by reaction with various inorganic and organic acids. These salts frequently provide convenient means for separating the product from the reaction mixture in which it is produced or from the solvent in which it is extracted in view of their insolubility in various media. Thus the product may be precipitated in the form of an insoluble salt and converted, by conventional techniques, to the free base or to another soluble or insoluble salt as desired.

Illustrative salts include the hydrohalides, such as hydrochloride, hydrobromide and hydroiodide, especially the first two, other mineral acid salts such as phosphate, sulfate, nitrate, etc., organic acid salts such as oxalate, tartrate, malate, maleate, citrate, pamoate, fumarate, camphorsulfonate, methanesulfonate, benzenesulfonate, toluenesulfonate, salicylate, benzoate, ascorbate, mandelate, or the like.

The compounds of formula I also form quaternary ammonium salts with lower alkyl halides, for example, methyl bromide, ethyl bromide and propyl iodide; benzyl halides, such as benzyl chloride; and dilower alkyl sulfates, such as dimethyl sulfate. To form the quaternary ammonium salts, the free base initially formed is interacted with at least one equivalent of the desired alkylating agent.

Formula I includes all stereoisomers and mixtures thereof. Thus, Formula I includes compounds of the structure:

(A) 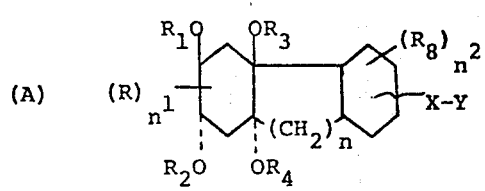

wherein all four OR groups are axial and $R_1O$ and $R_2O$ are in trans configuration and $OR_3$ and $OR_4$ are in trans configuration.

(B) 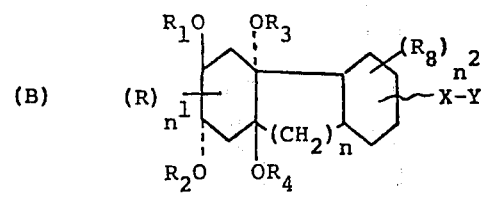

wherein $R_1O$ and $R_2O$ are in trans configuration, and $OR_3$ and $OR_4$ are in trans configuration and $R_3O$ and $R_4O$ are diaxial and $R_1O$ and $R_2O$ are diequatorial.

(C) 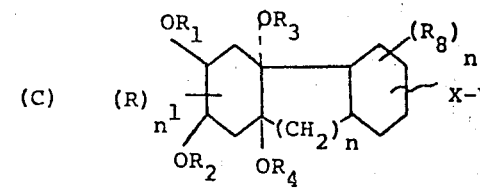

wherein $R_1O$ and $R_2O$ are in cis configuration and $OR_3$ and $OR_4$ are in trans configuration and one of $R_1O$ and $R_2O$ is equatorial and the other axial and $OR_3$ and $OR_4$ are diaxial.

(D) 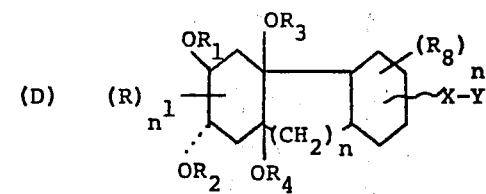

wherein $R_1O$ and $R_2O$ are in trans configuration and $OR_3$ and $OR_4$ are in cis configuration and $R_1O$ and $R_2O$ are diequatorial or diaxial and one of $OR_3$ and $OR_4$ is equatorial and the other axial.

(E) 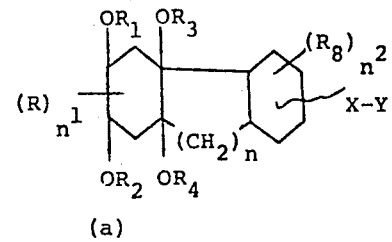

(a)

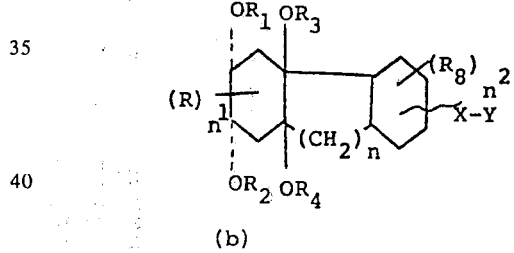

(b)

wherein in (a) $R_1O$ and $R_2O$ are in cis configuration and $OR_3$ and $OR_4$ are in cis configuration and the pair of $R_1O$ and $R_2O$ and the pair of $OR_3$ and $OR_4$ are in cis configuration and wherein in (b) $R_1O$ and $R_2O$ are in cis configuration and $OR_3$ and $OR_4$ are in cis configuration and the pair of $R_1O$ and $R_2O$ and the pair of $OR_3$ and $OR_4$ are in trans configuration.

In each of (A) through (E) ⁓X-Y can be up or down. Furthermore, each of (A) through (E) includes compounds wherein R and -X-Y are in trans configuration or cis configuration and R and $R_8$ are in trans configuration or cis configuration. Furthermore, the ring juncture as indicated below by the circled portion may be cis or trans.

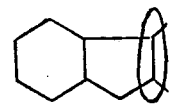

Examples of compound falling within the present invention are set out in Table A below:

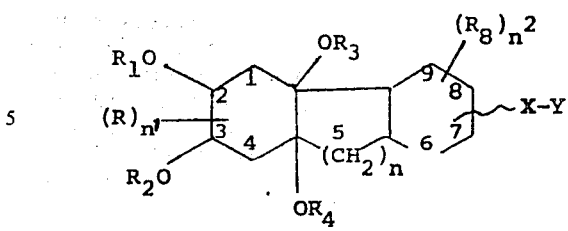

Table A

| | R | n¹ | $R_1$ | $R_2$ | $R_3$ |
|---|---|---|---|---|---|
| 1. | H | — | H | H | H |
| 2. | H | — | H | H | H |
| 3. | H | — | H | H | H |
| 4. | H | — | H | H | H |
| 5. | H | — | H | H | H |
| 6. | H | — | H | H | H |
| 7. | H | — | H | H | H |
| 8. | 3-$CH_3$ | 1 | H | H | H |
| 9. | 2-$C_2H_5$ | 1 | H | H | H |
| 10. | 1-$C_4H_8$ | 1 | $H_3CC(O)-$ | $H_3CC(O)-$ | $H_3CC(O)-$ |
| 11. | 4-$C_2H_5$ | 1 | $H_3CC(O)-$ | $H_3CC(O)-$ | $H_3CC(O)-$ |
| 12. | 2-⟨S⟩ | 1 | $H_3CC(O)-$ | $H_3CC(O)-$ | $H_3CC(O)-$ |
| 13. | 3-⟨S⟩ | 1 | $H_3CC(O)-$ | $H_3CC(O)-$ | H |
| 14. | H | — | $H_3CC(O)-$ | $H_3CC(O)-$ | H |
| 15. | H | — | $C_6H_5C(O)-$ | $C_6H_5C(O)-$ | H |
| 16. | H | — | $H_3CC(O)-$ | $H_3CC(O)-$ | $H_3CC(O)-$ |
| 17. | H | — | H | H | $-COC_2H_5$ |
| 18. | H | — | $H_3CC(O)-$ | H | $H_3CC(O)-$ |
| 19. | H | — | H | H | H |
| 20. | H | — | H | H | H |
| 21. | 2-$C_4H_9$ | 1 | H | H | H |
| 22. | 3-$C_3H_7$ | 1 | H | H | H |
| 23. | H | — | H | H | H |
| 24. | H | — | $H_3C-$ | $H_3C-$ | H |
| 25. | H | — | $H_3C-$ | $H_3C-$ | $H_3C-$ |
| 26. | H | — | $H_3C-$ | $H_3C-$ | $H_3C-$ |
| 27. | H | — | $H_5C_2-$ | $H_5C_2-$ | $H_5C_2-$ |
| 28. | H | — | $ClH_4C_2-$ | $ClH_4C_2-$ | $ClH_4C_2-$ |
| 29. | H | — | $BrC_2H_4$ | $BrC_2H_4$ | $CH_2Br$ |
| 30. | H | — | $(CH_3)_2NC(O)-$ | $(CH_3)_2NC(O)-$ | $(CH_3)_2NC(O)-$ |
| 31. | H | — | $(C_2H_5)_2NC(O)-$ | $(C_2H_5)_2NC(O)-$ | $(C_2H_5)_2NC(O)-$ |
| 32. | H | — | $C_2H_5OC(O)-$ | $C_2H_5OC(O)-$ | $C_2H_5OC(O)-$ |
| 33. | H | — | $CH_3OC_2H_4-$ | $CH_3OC_2H_4-$ | $CH_3OC_2H_4-$ |
| 34. | H | — | H | H | H |
| 35. | H | — | H | H | H |
| 36. | H | — | $CH_3C(O)$ | $CH_3C(O)$ | $CH_3C(O)$ |
| 37. | H | — | $(CH_3)_2CHC(O)-$ | $(CH_3)_2CHC(O)-$ | $(CH_3)_2CHC(O)-$ |
| 38. | H | — | H | H | H |
| 39. | H | — | $CH_3C(O)$ | $CH_3C(O)$ | $CH_3C(O)$ |
| 40. | H | — | H | H | H |
| 41. | H | — | $CH_3C(O)$ | $CH_3C(O)$ | $CH_3C(O)$ |
| 42. | H | — | $CH_3C(O)$ | $CH_3C(O)$ | $CH_3C(O)$ |
| 43. | H | — | H | H | H |

| $R_4$ | n | $R_8$ | $n^2$ | X-Y (position) |
|---|---|---|---|---|

Table A-continued

| | R | n¹ | R₁ | R₂ | R₃ |
|---|---|---|---|---|---|
| 1. | H | 1 | — | 0 | (7 or 8)—N(pyrrolidine) |
| 2. | H | 1 | — | 0 | (8)-(CH₂)₃—N(piperidine) |
| 3. | H | 1 | 9-CH₃ | 1 | (8)-CH₂)₃—N(piperidine) |
| 4. | H | 1 | — | 0 | (8)-CH₂—CH(CH₃)—N(morpholine) |
| 5. | H | 1 | — | 0 | (8)-(CH₂)₃—N(piperidine) |
| 6. | H | 1 | 8-S | 1 | (7)-N(piperidine) |
| 7. | H | 1 | — | 0 | (7)-(CH₂)₂—N(piperidine) |
| 8. | H | 1 | 7-HO— | 1 | (8)-(CH₂)₂—N(piperazine)N—CH₃ |
| 9. | H | 1 | — | 0 | (5a)-(CH₂)₂—N(piperidine) |
| 10. | H₃CC(=O)— | 1 | 9-CH₂C(=O)CH₂— | 1 | (8)-(CH₂)₃—N(pyrrolidine) |
| 11. | H₃CC(=O)— | | — | 0 | (7 or 8)-N(pyrrolidine) |
| 12. | H₃CC(=O)— | 1 | — | 0 | (8)-(CH₂)₃—N(morpholine) |
| 13. | H | 1 | — | 0 | (8)-(CH₂)₅—N(piperidine) |
| 14. | H | 1 | — | 0 | (8)-(CH₂)₃—N(morpholine) |
| 15. | H | 1 | — | 0 | (7)-N(piperidine) |
| 16. | H | 1 | — | 0 | (7)-N(piperidine) |
| 17. | H | 1 | — | 0 | (9a)-N(piperidine) |
| 18. | H | 1 | — | 0 | (7)-N(piperidine) |
| 19. | H | 1 | — | 0 | (6)-N(piperidine) |
| 20. | H | 1 | 8-CH₃<br>7-CH₃ | 2 | (9)-CH₂CH₂—N(piperidine) |
| 21. | H | 1 | — | — | (8)-NH₂ |
| 22. | H | 1 | — | 0 | (8)-(CH₂)₂N(CH₃)₂ |
| 23. | H | 1 | — | 0 | (8)-(CH₂)₃—CH(CH₃)—N(piperidine-C₂H₅) |

Table A-continued

| R | n¹ | R₁ | R₂ | R₃ |
|---|---|---|---|---|
| 24. H | 1 | — | 0 | (5a)-(CH₂)₂N(CH₃)₂ |
| 25. H₃C— | 1 | — | 0 | (8)-(CH₂)₃—CH(CH₃)—N(piperidinyl) |
| 26. H₃C— | 1 | — | 0 | (8)-(CH₂)₂—N(pyrrolidinyl) |
| 27. H₅C₂— | 1 | — | 0 | (7)-(CH₂)₃N(C₂H₅)₂ |
| 28. ClH₄C₂— | 1 | — | 0 | (9a)-(CH₂)—N(piperidinyl) |
| 29. CH₂Br | 1 | — | 0 | (8)-(CH₂)₃—N(piperidinyl) |
| 30. (CH₃)₂NC(O)— | 1 | — | 0 | (8)-(CH₂)₃—N(morpholinyl) |
| 31. (C₂H₅)₂NC(O)— | 1 | — | 0 | (7)-(CH₂)₂—N(pyrrolidinyl) |
| 32. C₂H₅OC(O) | 1 | — | 0 | (8)-(CH₂)₃—NH₂ |
| 33. CH₃OC₂H₄— | 1 | — | 0 | (8)-(CH₂)₃—N(piperidinyl) |
| 34. H | 2 | — | 0 | (9)-(CH₂)₃—N(piperidinyl) |
| 35. H | 2 | — | 0 | (8)-(CH₂)₃—N(piperidinyl) |
| 36. CH₃C(O) | 2 | — | 0 | (9)-(CH₂)₃N(piperidinyl) |
| 37. (CH₃)₂CHC(O)— | 2 | — | 0 | (7)-(CH₂)₃N(piperidinyl) |
| 38. H | 1 | — | 0 | (7)-N(pyrrolidinyl) |
| 39. CH₃C(O) | 1 | — | 0 | (7)-N(pyrrolidinyl) |
| 40. H | 1 | — | 0 | (8)-N(pyrrolidinyl) |
| 41. CH₃C(O) | 1 | 5a-OH | 1 | (8)-N(pyrrolidinyl) |
| 42. CH₃C(O) | 1 | 8-CH₃CO(CH₂)₂— | 1 | (6)-(CH₃)₂NHCH₃ |
| 43. H | 1 | 8-OH, 7-OH | 2 | (6)-(CH₃)₂N(CH₃)₂ |

Each of the above structures represent each of the possible isomers as outlined hereinbefore as well as mixtures of such isomers.

METHODS OF PREPARATION

Further, in accordance with the present invention, a process is provided for preparing the compounds of Formula I of the invention, which comprises forming a diene of the structure

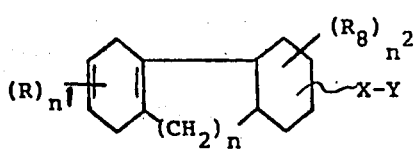

and converting the diene to the tetrol or tetrol derivatives of Formula I.

The tetrol (Type A) wherein $R_1$, $R_2$, $R_3$ and $R_4$ are hydrogen, can be formed by hydroxylating the diene to the corresponding tetrol, for example, by reacting the diene with formic acid and aqueous hydrogen peroxide, at temperatures ranging from about 20° to about 40°C. to form a mixture of esters, and then subjecting the mixture of esters to basic hydrolysis by dissolving the mixture of esters in a solvent boiling below about 100°C., such as a monohydric alcohol containing up to four carbon atoms (e.g., methyl alcohol, ethyl alcohol, propyl alcohol, isopropyl alcohol or butyl alcohol), and then treating the solution with a base, such as an alkali metal or alkaline earth metal hydroxide or alkoxide (e.g., sodium hydroxide, potassium hydroxide, barium hydroxide, calcium hydroxide, sodium methoxide or calcium diethoxide) and heating the mixture to temperatures ranging from about 40° to about 80°C., to form a tetrol (Type A) of the structure:

III 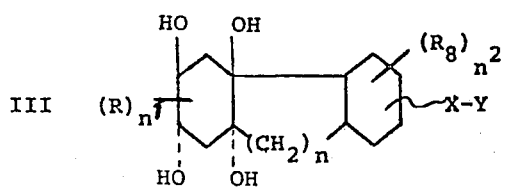

wherein all hydroxyl groups are axial.

In the above reaction the hydrogen peroxide is employed in a molar ratio to the diene of within the range of from about 3.2:1 to about 15:1 and preferably from about 3.2:1 to about 5:1. The base is employed in a molar ratio to the mixture of esters of within the range of from about 3.2:1 to about 10:1 and preferably from about 3.2:1 to about 5:1.

The Type(A)tetrol of Formula III can be converted to the corresponding tetra ester, i.e., where $R_1$, $R_2$, $R_3$ and $R_4$ are acyl as defined hereinbefore, by reacting the tetrol with an acylating agent, such as a hydrocarbon carboxylic acid containing less than twelve carbon atoms as discussed hereinbefore, the acid anhydride thereof, or corresponding acyl halide, and an acid catalyst, such as perchloric acid, at a temperature within the range of from about −20 to about 0°C. The acid, acid anhydride or acyl halide is employed in a molar ratio to the tetrol of within the range of from about 4:1 to about 20:1 and preferably from about 4:1 to about 10:1 and the acid catalyst is employed in a molar ratio to the tetrol of within the range of from about 1.1:1 to about 2:1 and preferably from about 1.1:1 to about 1.5:1.

The tetrol of Formula III can be converted to the corresponding diester wherein $R_1$ and $R_2$ are acyl and $R_3$ and $R_4$ are hydrogen, by dissolving the tetrol in an organic base, such as pyridine, and treating the solution with an acylating agent such as an acid anhydride (as described hereinbefore) or corresponding acyl halide in a molar ratio of acylating agent:tetrol of within the range of from about 2.1:1 to about 10:1 and preferably from about 2.2:1 to about 6:1, while maintaining the reaction mixture at a temperature within the range of from about 0° to about 20° and preferably from about 5° to about 15° to form a diester of the structure IV 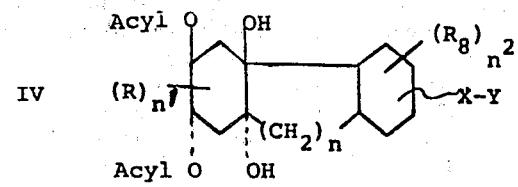

The Type A tetrol III can be converted to the corresponding triester wherein $R_1$, $R_2$ and $R_3$ are acyl and $R_4$ is hydrogen and X is preferably a single bond, where the nitrogen atom of Y is suitably located to participate in the acylation, by mixing the tetrol with a base, preferably pyridine, and reacting the mixture with an acylating agent such as an acid anhydride or corresponding acyl halide (as defined herebefore) in a molar ratio of acylating agent:tetrol of within the range of from about 3:1 to about 10:1 and preferably from about 3:1 to about 5:1, at a temperature of within the range of from about 5° to about 40° and preferably from about 10° to about 30° to form a triester of the structure:

V 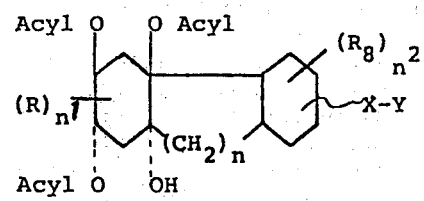

The above triester can be converted to the corresponding diester of the structure:

VI 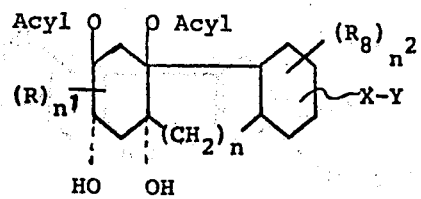

by treating the triester with an alcohol-water mixture in a volume ratio of alcohol:water within the range of from about 9:1 to about 1:1 and preferably from about 1:1 to about 3:1. The alcohol-water mixture is employed in a weight ratio to the triester of within the range of from about 10:1 to about 100:1 and preferably from about 10:1 to about 50:1.

The tetrol III can be converted to the corresponding monoester wherein $R_3$ is acyl and $R_1$, $R_2$ and $R_4$ are hydrogen by treating the tetrol with a haloalkyl carbonate in a molar ratio of carbonate:tetrol of within the range of from about 1.1:1 to about 100:1 and preferably from about 10:1 to about 50:1 at a temperature within the range of from about 20° to about 60° and preferably from about 25° to about 35° to form a monoester of the structure:

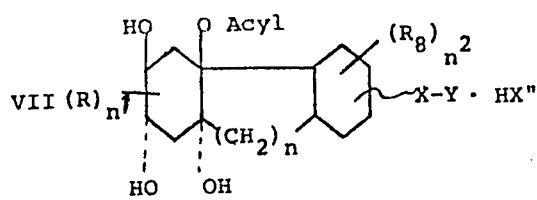

wherein X'' is a halogen.

In an alternative procedure, the diene of formula II can be converted to the corresponding tetrol by dissolving the diene II in an organic carboxylic acid having up to about eight carbon atoms, such as acetic acid, treating the mixture with a silver salt corresponding to the acid, such as silver acetate (in a molar ratio of diene to silver salt of within the range of from about 1:2 to about 1:4 and preferably about 1:2) and iodine (in a molar ratio of diene to iodine of 1:1), heating the reaction mixture at a temperature of within the range of from about 60° to about 110° and preferably from about 80° to about 100°, to form a diester (depending on which acid and silver salt are employed) of the structure:

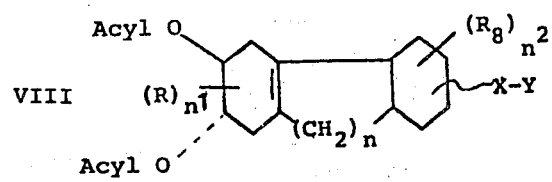

The above diester of the structure VIII can be converted to the corresponding tetrol of Type (A) by dissolving the diester in a suitable protonic solvent, such as ethyl alcohol, treating the solution with an excess of an aqueous base, such as aqueous sodium hydroxide or potassium hydroxide, to effect hydrolysis to the corresponding diol of the structure:

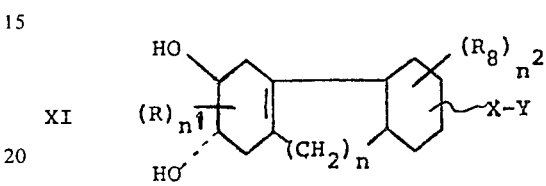

The above diol can be converted to the tetrol by reacting the dial with formic acid and hydrogen peroxide (as described hereinbefore), at temperatures ranging from about 20° to about 40°C., preferably about 35°, and then treating the mixture (free of solvent) with an alcohol and a base (as described hereinbefore) to form the tetrol wherein all OR's are axial and each pair of OR's are trans. (Type (A)).

The tetrol isomer or derivatives thereof of Type (A) can also be prepared by reacting the diene II with formic acid and one equivalent of an oxidizing agent, such as aqueous hydrogen peroxide, and after removal of solvent, dissolving the residue in an alcohol-base as described hereinbefore to effect hydrolysis and form a diol olefin of the structure:

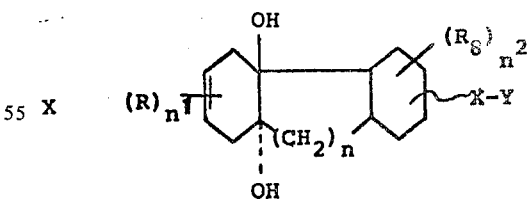

The above diol olefin can then be converted to the tetrol of type (A) as described hereinbefore with respect to the conversion of the diol olefin IX.

Where Y is 

and at least one of $R_5$ and $R_6$ is or includes an aromatic ring, the Type (A) tetrols of the invention can be prepared by reducing a hydroxyalkyl compound of the structure:

XI 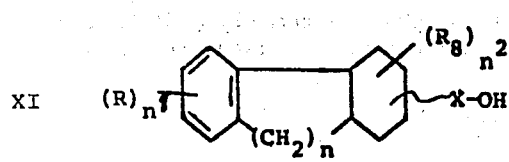

wherein X is lower alkylene as definied hereinbefore with respect to the corresponding diene, by reacting the indene with a reducing metal, such as lithium or sodium in liquid ammonia in the presence of a proton source such as a lower alcohol, to form the corresponding hydroxyalkyl diene of the structure:

XII 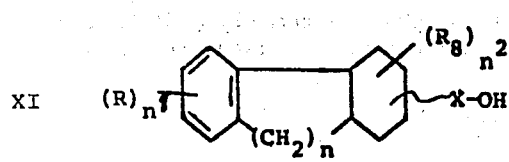

dissolving the hydroxyalkyl diene in a basic organic solvent, such as pyridine, cooling the solution to below 0°, treating the solution with a solution of p-toluenesulfonyl sulfonyl chloride in pyridine, in a molar ratio of diene to p-toluenesulfonyl sulfonyl chloride of within the range of from about 1:1 to about 1:1.5, and cooling to form the corresponding diene tosylate of the structure:

XIII

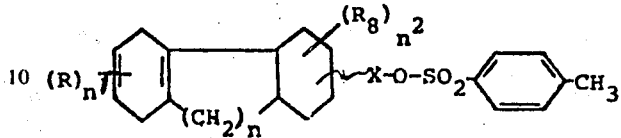

reacting the diene tosylate with an arylamine or substituted arylamine, aryl lower alkylamine or substituted aryl lower alkylamine or an amine of the structure

(in a molar ratio of tosylate to amine of within the range of from about 1:2 to about 1:5) in an aromatic solvent boiling below about 120°C., such as toluene or benzene to form an aminoalkyldiene of the structure:

XIV 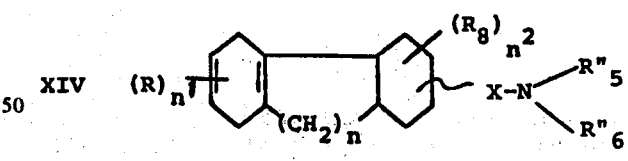

wherein $R''_5$ and $R''_6$ is the same or different and can be aryl, substituted aryl, arylalkyl, substituted arylalkyl or any of the $R_5$ and $R_6$ substituents mentioned previously. The substituted aryl groups can include any of the substituents set out hereinbefore with respect to the heterocyclic groups. The aminoalkyl diene can be converted to the corresponding tetrol by reacting the diene with formic acid and an oxidizing agent, such as hydrogen peroxide, removing solvent and subjecting the residue to basic hydrolysis (alcohol-base) as described hereinbefore, to form a tetrol of the structure:

XV 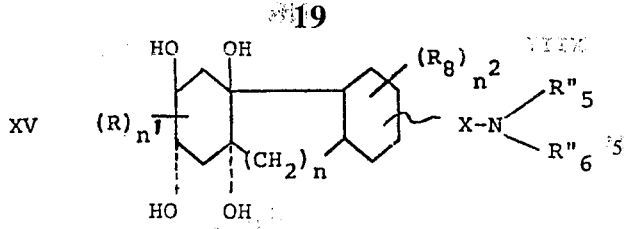

wherein R''₅ and R''₆ are as defined above. When R''₅ or R''₆ is benzyl it can be converted to a hydrogen atom by treating the tetrol with hydrogen in the presence of a catalyst for reduction, such as palladium on strontium carbonate.

Where Y is NH₂, the Type (A) tetrols of the invention can be prepared by reacting an aminoalkyl tricycle (prepared by reduction of the corresponding cyanoalkyl tricycle) or an animoalkyl bicyclic compound with a reducing agent, such as lithium ribbon in the presence of liquid ammonia, ethyl ether, and a proton source such as a lower alcohol, to form a diene of the structure:

XVI 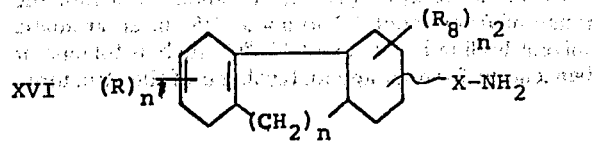

and reacting the diene with an acyl halide (wherein acyl and the halogen are as defined hereinbefore), such as benzoyl chloride, in a molar ratio of diene: halide of within the range of from about 1:1 to about 2:1 in a basic solvent, such as pyridine, triethylamine, or dilute base to form a diene of the structure:

XVII 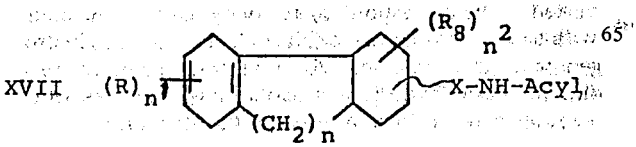

and reacting the diene with formic acid and an oxidizing agent, such as hydrogen peroxide, and subjecting the product to basic hydrolysis (as described hereinbefore) to form an aminoalkyl tetrol of the structure:

XVIII 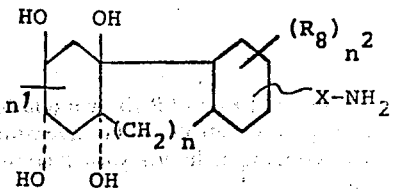

Preparation of Other Isomers (Types B,C,D and E) Tetrol isomers of Type (B) or esters thereof, that is:

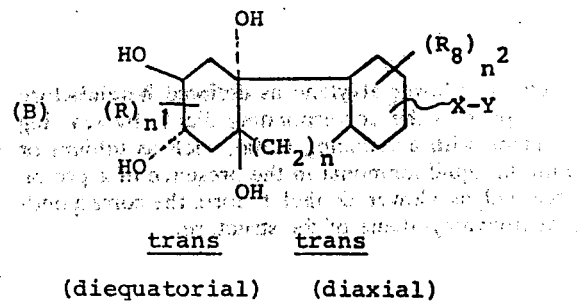

trans         trans
(diequatorial)   (diaxial)

can be prepared by treating a diester olefin of the structure:

VIII 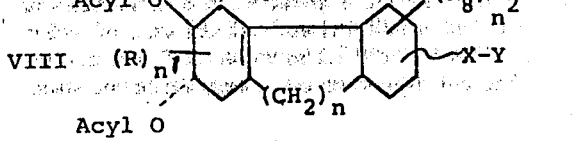

with formic acid and an oxidizing agent, such as hydrogen peroxide, at temperatures ranging from about 20 to about 40°C. and preferably from about 25° to about 35°C., and then treating the product with an alcohol-base, such as a monohydric alcohol and any of the bases mentioned hereinbefore and heating the mixture at temperatures ranging from about 40° to about 100° and preferably at reflux temperature to form a Type (B) tetrol.

Tetrol isomers of Type (C) of derivatives thereof having the formula:

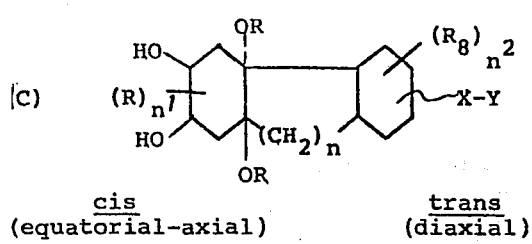

cis
(equatorial-axial)

trans
(diaxial)

XIX

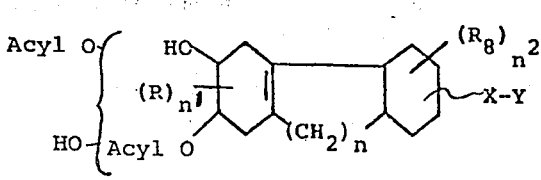

wherein X and Y are as defined hereinbefore (which is a novel intermediate).

The above monoalcohol monoester can be converted to the corresponding diol by basic hydrolysis, for example, by treatment with alcohol-base as described hereinbefore. The diol or the monoalcohol monoester can be converted to the Type(C) tetrol isomer by treating it with formic acid and an oxidizing agent, such as hydrogen peroxide and subsequently subjecting the resulting product to basic hydrolysis (all of which is described in detail hereinbefore in the preparation of the Type(A) isomer) to form the Type(C) tetrol isomer.

Tetrol isomers of Type (D) or esters thereof, that is:

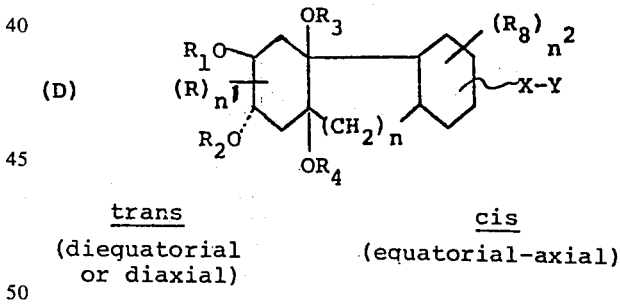

trans
(diequatorial
or diaxial)

cis
(equatorial-axial)

can be prepared by dissolving a diene of the structure:

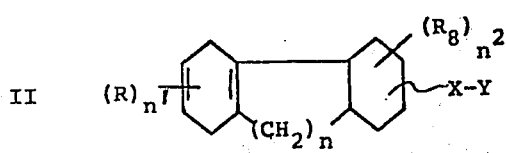

in an alkanoic acid containing from two to ten carbon atoms, such as acetic acid, containing from about 2 to about 10% water and preferably about 5% water, treating the solution with a silver salt corresponding to the acid, such as silver acetate and iodine in the same manner as described hereinbefore in the alternative procedure for preparing the Type(A) tetrol isomer, to form an olefin of the structure:

can be prepared by converting a diene of the structure II to the corresponding diester olefin of the structure:

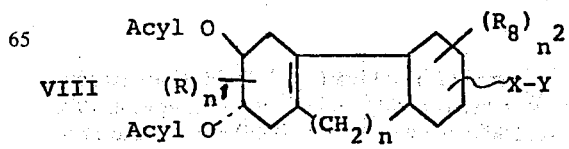

as described hereinbefore and then dissolving the diester olefin in a basic organic solvent, such as a mixture of pyridine and benzene, and treating the solution with osmium tetroxide in a molar ratio of O₅O₄ to diester olefin of within the range from about 1:1 to about 4:1 and preferably about 1:1, to form a Type(D) diester diol isomer of the structure:

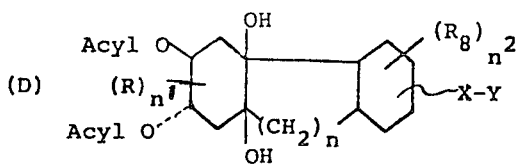

The Type(D) diester diol isomer can be converted to the Type(D) tetrol isomer by basic hydrolysis as described hereinbefore with respect to the Type(A) isomer.

Tetrol isomers of Type (E) or esters thereof, that is:

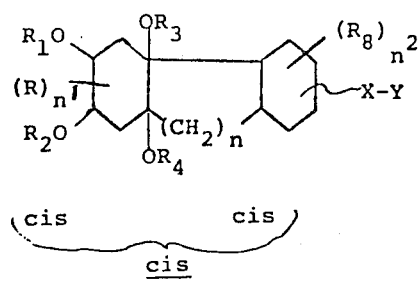

and

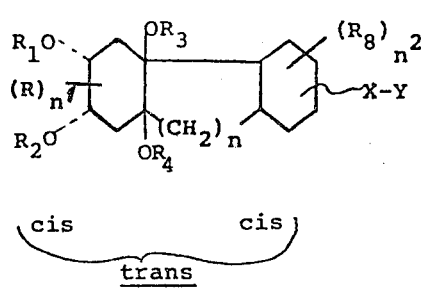

can be prepared by converting a diene of the structure II to the corresponding monoalcohol monoester of the structure XIX as described hereinbefore in the preparation of the Type (C) isomer, dissolving the monoalcohol monoester in a basic solvent, for example, pyridine, treating the solution with an acid anhydride of an alkanoic acid containing up to about 6 carbon atoms, such as acetic anhydride or acid anhydrides of any of the alkanoic acids mentioned hereinbefore, in a molar ratio of monoalcohol monoester to acid anhydride of within the range of from about 1:1 to about 1:5 and preferably from about 1:1 to about 1:2, to form a diester olefin of the structure:

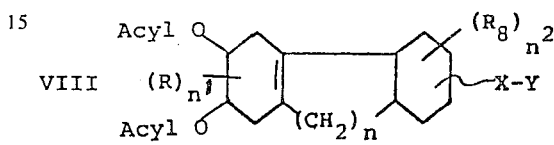

and then treating the diester olefin with pyridine and osmium tetroxide (as described hereinbefore in the preparation of the Type (D) isomer), to form a mixture of Type E diester diols of the structures:

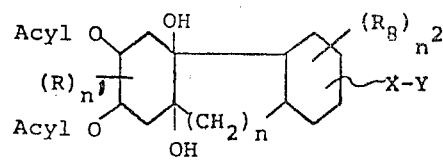

and

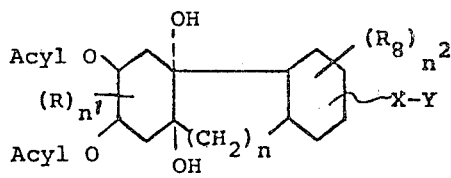

The diester diols can be converted to the corresponding Type (E) tetrols by basic hydrolysis as described hereinbefore in the preparation of the Type(A) isomers.

PREPARATION OF OTHER TETROL DERIVATIVES

The tetrol ethers of formula I wherein $R_1$, $R_2$, $R_3$ and $R_4$ are lower alkyl can be prepared by dissolving a tetrol of Formula I in a suitable nonprotonic solvent such as DMSO, dioxane, ethyl ether or tetrahydrofuran, adding to the solution at least four equivalents and preferably from about five to about seven equivalents of a metal hydride such as sodium hydride or sodium amide, thereafter adding to the mixture slowly with stirring about four equivalents of a lower alkyl halide such as methyl iodide, methyl bromide or ethyl iodide, and maintaining the temperature of the reaction mixture within the range of from about 20° to about 60°C. and preferably from about 30° to about 40°C., to form the tetrol ether. Thereafter, ethyl alcohol and/or water can be added to decompose excess base, and the tetrol ether can be recovered by stripping down the organic solvent.

Tetrols of Formula I wherein $R_1$, $R_2$, $R_3$ and $R_4$ are halo-lower alkyl can be formed as described hereinbefore with respect to the preparation of the tetrol ethers with the exception that an alkylene halohalide (or dihaloalkane) such as trimethylene chlorobromide or pentamethylene fluoro iodide, is employed in place of the alkyl halide.

Tetrols of Formula I wherein $R_1$, $R_2$, $R_3$ and $R_4$ are lower dialkylamino carbonyl can be formed as described hereinbefore with respect to the preparation of the tetrol ethers with the exception that a dialkyl carbamoyl halide, such as dimethyl carbamoyl chloride or diethyl carbamoyl bromide, or a substituted isocyanate such as an alkyl or aryl isocyanate is employed in place of the alkyl halide.

Tetrols of Formula I wherein $R_1$, $R_2$, $R_3$ and $R_4$ are lower alkoxyalkylene wherein the alkylene group contains two to five carbon atoms can be formed as described hereinbefore with respect to the preparation of the tetrol ethers except that an alkoxyalkylene halide such as ethoxypropyl chloride or ethoxyethyl bromide is employed in place of the alkyl halide.

Tetrols of Formula I wherein $R_1$, $R_2$, $R_3$ and $R_4$ are $$R-O-\overset{O}{\underset{\|}{C}}-$$

can be formed as described hereinbefore with respect to the preparation of the tetrol ethers except than an alkylhaloformate such as methylchloroformate or ethylchloroformate is employed in place of the alkyl halide.

INTERMEDIATE

The diester and diol olefin intermediates of the structures:

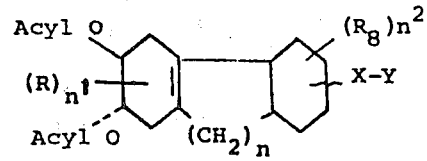

VIII

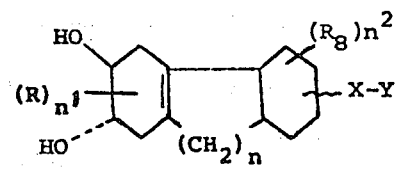

IX wherein acyl and X and Y are as defined hereinbefore are novel intermediates. Examples of such diesters of diol-olefins include, but are not limited to, the following set out in Table B below:

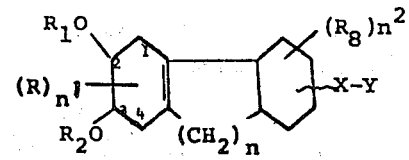

Table B

| R | $n^1$ | $R_1$ | $R_2$ | n | $R_8$ | $n^2$ | X-Y |
|---|---|---|---|---|---|---|---|
| 1. H | — | $CH_3\overset{O}{\underset{\|}{C}}-$ | $CH_3\overset{O}{\underset{\|}{C}}-$ | 1 | — | 0 | 8-$NH_2$ |
| 2. H | — | $C_4H_9\overset{O}{\underset{\|}{C}}-$ | $C_4H_9\overset{O}{\underset{\|}{C}}-$ | 1 | — | 0 | 7-$NH_2$ |
| 3. H | — | $C_6H_{13}C-$ | $C_6H_{13}C-$ | 1 | — | 0 | 7-$(CH_2)_3$—N⟨⟩N—$(CH_2)_2OH$ |
| 4. H | — | $CH_3C-$ | $C_2H_5C-$ | 1 | — | 0 | 8-$CH_2$—$NHCH_3$ |
| 5. 2-$CH_3$ | 1 | H | H | 1 | — | 0 | 8-$NH_2$ |
| 6. 3-$C_2H_5$ | 1 | H | H | 1 | 7-$CH_3$ | 1 | 8-N⟨⟩ |
| 7. 2-⟨S⟩ | 1 | H | H | 1 | 8-⟨S⟩ | 1 | 9-$CH_2\overset{CH_3}{\underset{\|}{CH}}$—N⟨⟩ |
| 8. H | — | H | H | 1 | 6-OH | 1 | 7-$(CH_2)_2$— N⟨⟩N —$(CH_2)_2OH$ |
| 9. H | — | H | H | 1 | — | 0 | 8-$(CH_2)_2$—N⟨O⟩ |
| 10. H | — | H | H | 1 | 8-$HOCH_2$— | 1 | 7-$(CH_2)_3\overset{CH_3}{\underset{\|}{CH}}$—N⟨⟩ |

Table B-continued

| R | n¹ | $R_1$ | $R_2$ | n | $R_H$ | $n^2$ | X-Y |
|---|---|---|---|---|---|---|---|
| 11. 2-$C_4H_9$ | 1 | H | H | 2 | — | 0 | 9-$(CH_2)_3$—N⟨⟩ |
| 12. 2,3-di-$CH_3$ | 2 | H | H | 2 | — | 0 | 8-$(CH_2)_3$N⟨] |
| 13. H | — | $CH_3\overset{O}{\overset{\|}{C}}$— | $CH_3\overset{O}{\overset{\|}{C}}$— | 1 | — | 0 | 8-N⟨⟩O |
| 14. H | — | $C_3H_7\overset{O}{\overset{\|}{C}}$ | $C_3H_7\overset{O}{\overset{\|}{C}}$ | 1 | — | 0 | 9-N⟨] |

The diol-olefins of the structure X that is

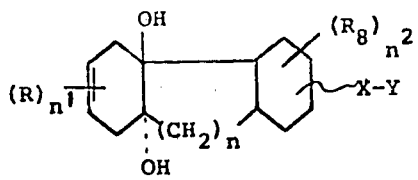

wherein X and Y are defined hereinbefore are novel intermediates.

Typical examples of diol olefins of the structure X correspond to the tetrols and esters and the diester and diol-olefins of structure VIII and IX set out hereinbefore.

STARTING MATERIALS

The diene starting material:

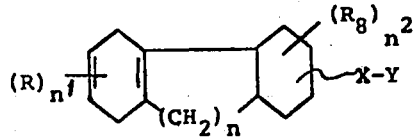

XX can be prepared by the Birch reduction of an aromatic precursor of the structure:

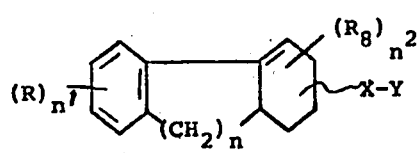

XXI

Aromatic precursors of the structure XXV

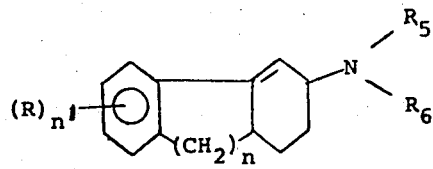

XXV can be prepared by reacting a compound of the structure

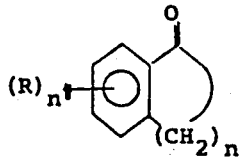

XXVI with a compound of the structure XXVII

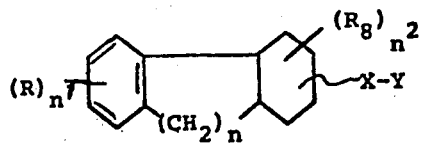

XXIII or 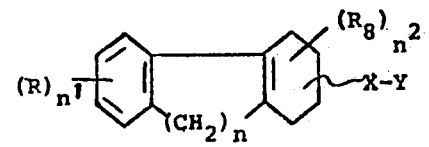

XXIV

XXVII 

in a molar ratio of XXVI:XXVII of within a range of from about 1:1 to about 10:1 and preferably from about 1.2:1 to about 2.5:1, at a temperature within the range from about 20° to about 120° and preferably from about 80° to about 110°, in the presence of a hydrocarbon solvent, such as benzene, toluene or xylene and an acid such as p-toluenesulfonic acid or titanium tetrachloride, the reaction being conducted in the absence of oxygen, to form a compound of the structure XXVIII XXVIII 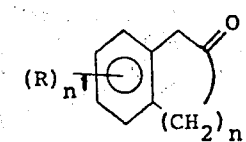

Compound XXVIII is reacted with methyl vinyl ketone, in the absence of oxygen, in a molar ratio of XXVIII:ketone within the range of from about 1:1 to about 10:1 and preferably from about 1:1 to about 3:1, in a hydrocarbon solvent as mentioned above to form a compound of the structure XXIX

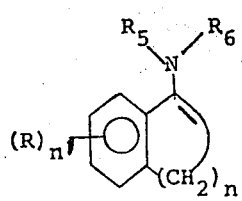

XXIX

Compound XXIX is then dissolved in an alkanol solvent, such as methanol, and reacted with sodium borohydride at a temperature within the range of from about 20° to about 50° and preferably from about 25° to about 35° to form the aromatic precursor, that is compound XXV.

An isomer of compound XXV, namely XXX

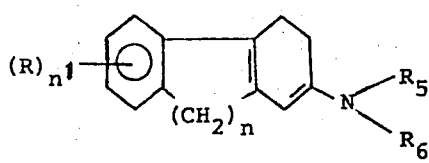

XXX can be prepared as outlined above with respect to compound XXV with the exception that the starting material employed is of the structure XXXI XXXI 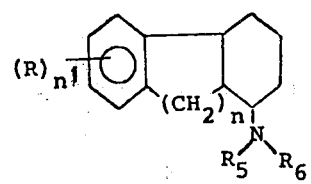

Other isomers of the structures XXXII and XXXIII

XXXII 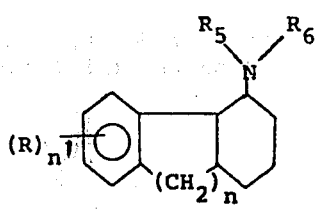

XXXIII 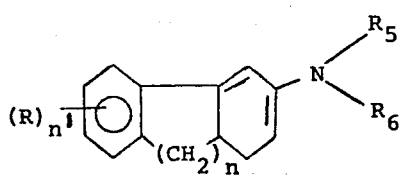

can be prepared from ketones known in the art and having the structures XXXIV and XXXV XXXIV 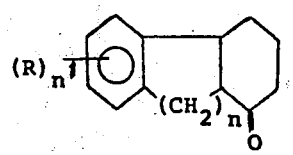

XXXV 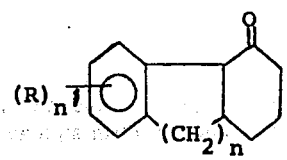

employing procedures known in the art, such as conversion to the enamine as described hereinbefore and reduction of the enamine with, for example, sodium borohydride.

Aromatic precursors of the structure

XXXVI 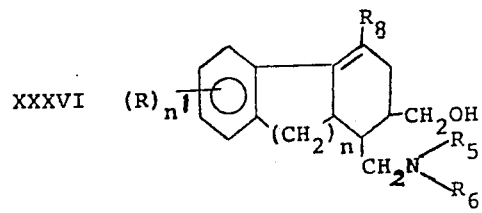

wherein $R_8$ is hydrogen, alkyl or cycloalkyl can be prepared by reaction of a compound of the structure XXXVII 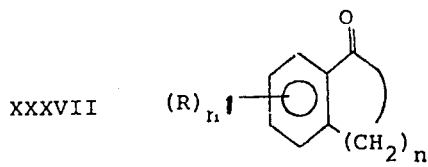

with a Grignard reagent of the structure

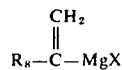

wherein X is Br or I, and $R_8$ is hydrogen, alkyl or cycloalkyl, or dialkylaminoalkyl to form a compound of the structure XXXIX 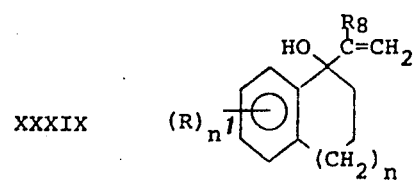

Compound XXXIX is refluxed with a mixture of maleic anhydride and acetic anhydride or isopropenyl acetate to form an anhydride of the structure XL 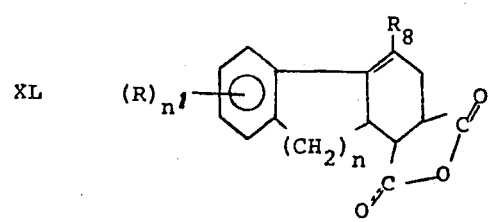

Anhydride XL is then refluxed with an alkanol, for example, methanol, to form an acid of the structure XLI 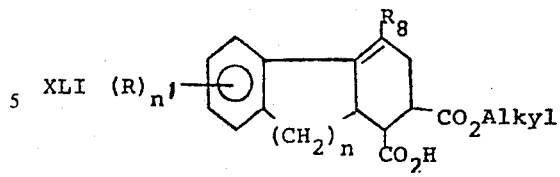

Acid XLI is converted to its acid halide by reacting it with an acid halide, for example, oxalyl chloride, and the resulting acid halide is reacted with an amine compound of the structure XXVII to form an ester of the structure XLII 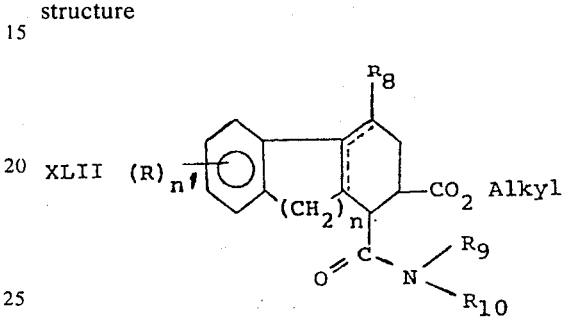

wherein the dashed bonds indicate a double bond at one or the other positions as shown, as well as mixtures of these isomers.

Compound XLII can then be reduced, for example, by reaction with lithium aluminum hydride, to form a compound of the structure XLIII 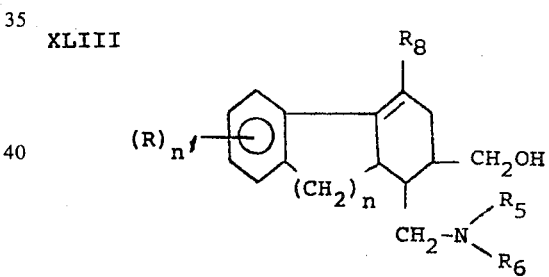

The isomer of compound XLIII having the structure

XLIV 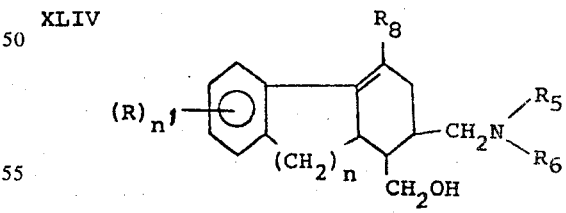

can be prepared by reacting the compound of the structure XL with an amine of the structure XXVII to form a compound of the structure XLV XLV 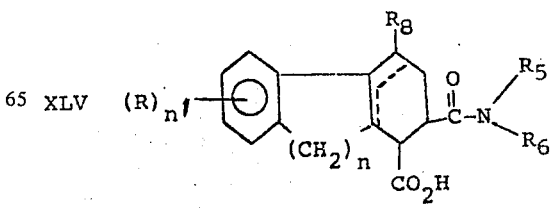

Compounds XLV can then be reduced with lithium aluminum hydride in the presence of tetrahydrofuran and dioxane to form a compound of the structure XLVI 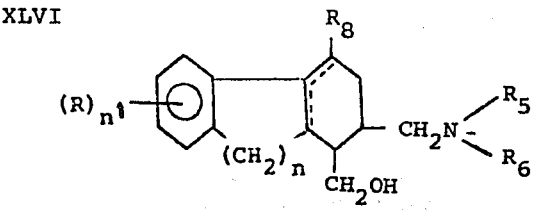

In each of the above structures as well as those that follow the dashed double bonds indicate a double bond at one position or the other, as well as mixtures of these isomers.

Compounds of the structure

XLVII 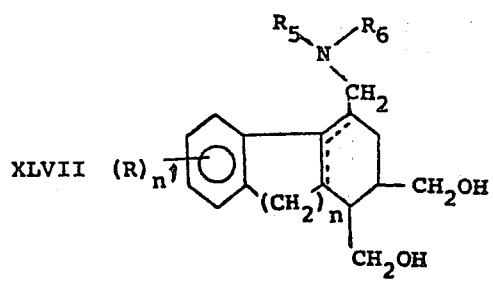

can be prepared by reacting an anhydride of the structure XL with lithium aluminum hydride.

Compounds of the structure XLIX

XLIX 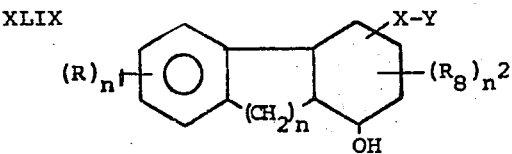

can be prepared by reacting a starting material of the structure

L 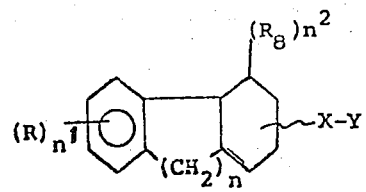

with a hydroborating agent such as diborane in the presence of an oxidizing agent, such as hydrogen peroxide, and a base such as an alkali metal hydroxide.

Compounds of the structure

LI 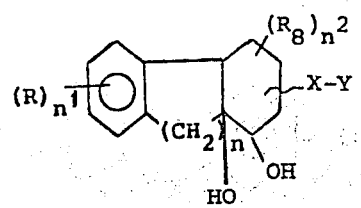

can be prepared by reacting compound L with formic acid and an oxidizing agent, such as hydrogen peroxide.

Furthermore, compounds of the structure

LII 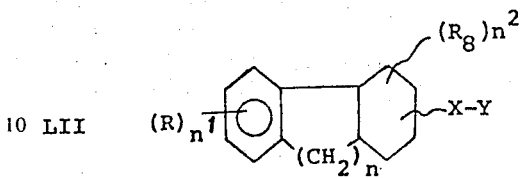

can be prepared by reacting compounds of the structure

LIII 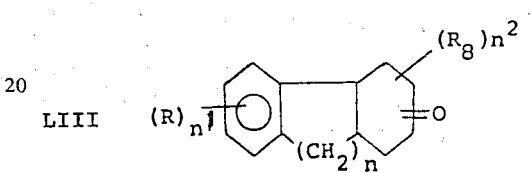

with an amino alkyl Grignard reagent to form compounds of the structure

LIIIA 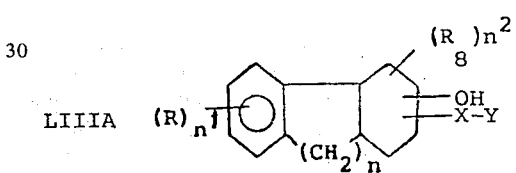

where Y is dialkylamino and this is dehydrated and reduced employing procedures known in the art.

An aromatic precursor of the structure:

LIV 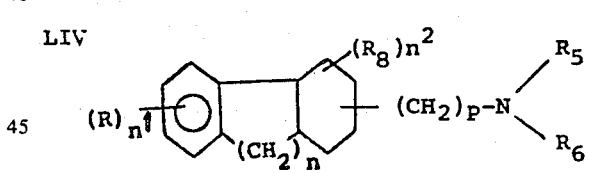

can be prepared by reacting a compound of the structure:

LV 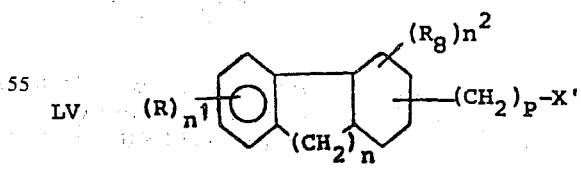

wherein X' is a reactive halogen or other displaceable group such as tosylate and p is 1 to 10, with an amino compound of the structure:

XXVII 

wherein $R_5$ and $R_6$ are as defined hereinbefore, in a molar ratio of LV:amine of within the range of from about 1:2 to about 1:10 and preferably from about 1:2 to about 1:4, at a temperature within the range of from about 75° to about 150° and preferably from about 100° to about 120°, in the presence of a solvent having a boiling point below about 150°C, such as toluene or xylene.

Aromatic precursors of the structure LIV where $p$ is 1, $n$ is 1 or 2 and $R_8$ is hydrogen that is LVII 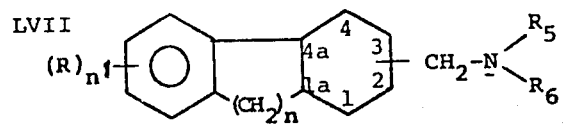

wherein the aminomethylene group may be at the 1a-, 4a-, 1-, 2-, 3- or 4-position of the ring, and $R_5$ and $R_6$ are as defined hereinbefore except that they are other than aromatic, can be prepared as follows: a fluorene-carboxylic acid of the structure LVIII 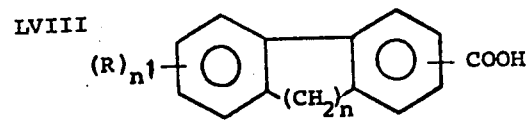

where the carboxyl is on the 1-, 2-, 3- or 4-position, is reduced by reacting such acid in a solvent such as a lower alcohol, for example, ethanol, with liquid ammonia and lithium and thereafter evaporating off the ammonia, acidifying, and reducing over a catalyst for reduction such as $PtO_2$ or Pd/C, under hydrogen, to form an acid of the structure LIX 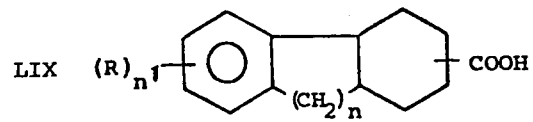

The above acid as well as acids of the structure

LIXa 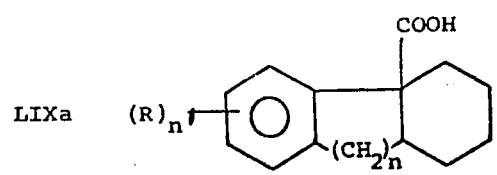

which are known in the art can then be converted to its corresponding acid halide for example by reacting the acid with thionyl chloride. The acid halide is reacted with an amine

in the presence of a non-polar solvent such as benzene or hexane to form an amide of the structure LX 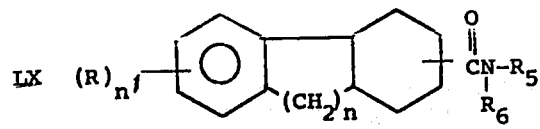

which is converted to the corresponding amine of structure LVII, by reduction with, for example, lithium aluminum hydride.

Aromatic precursors of the structure LIV where $p$ is 2, $n$ is 1 or 2 and $R_8$ is hydrogen, that is LXI 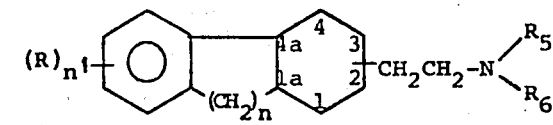

where the aminoethyl group may be at the 1a-, 4a-, 1-, 2-, 3- or 4-position, can be prepared by reacting a hexahydrofluorene carboxylic acid of the structure LIX or LIXa with lithium aluminum hydride to form an alcohol of the structure LXII 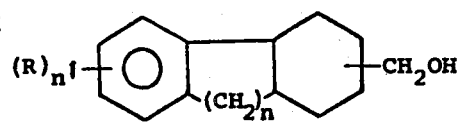

which is reacted with phosphorus tribromide in the presence of a base such as pyridine to form the corresponding bromide LXIII 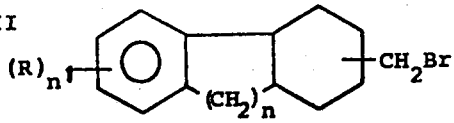

The bromide is dissolved in a solvent, such as mixtures of t-butanol and N-methyl-2-pyrrolidone and treated with an alkali metal cyanide, such as potassium cyanide, to form the corresponding acetonitrile LXIV 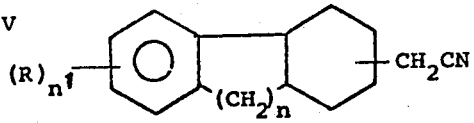

which is reacted with lithium aluminum hydride to form an ethylamine of the structure LXV 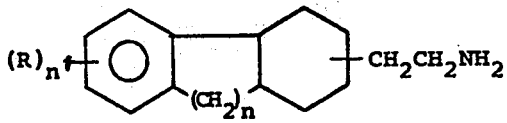

The above amine can be converted to $R_5,R_6$-substituted amines of structure LXI employing conventional techniques.

Aromatic precursors of the structure LIV where p is 3 to 10 and $R_8$ is hydrogen, that is

LXVI

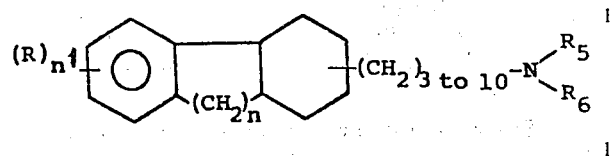

can be prepared by reacting a hexahydro-fluorene-one of the structure

LXVII 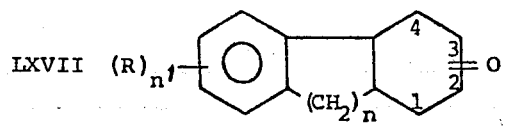

wherein =O is in the 1-, 2-, 3- or 4-position with a Grignard reagent of the structure LXVIII 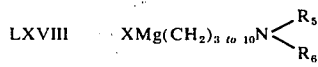

to form a compound of the structure

LXIX

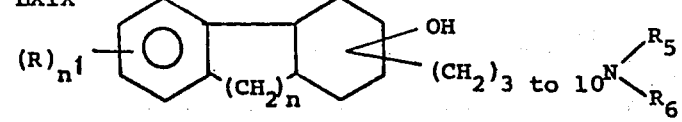

the hydroxyl being attached to the same carbon as the aminoalkylene group, which is treated with thionyl chloride and base (where $n$ is 1) or with acid (where $n$ is 2) to form an olefin of the structure

LXX

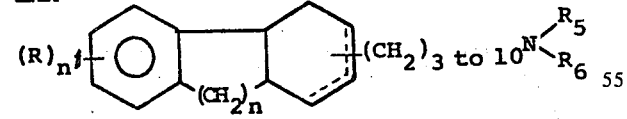

the broken lines indicating a double bond at either position, which is reduced, for example, by reaction with hydrogen over $PtO_2$, to form the formula LXVI compound.

Aromatic precursors of the structure

LXXI 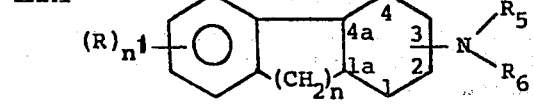

wherein the amino group can be at the 1-, 2-, 3- or 4-position can also be prepared by reacting a ketone of the structure LXVI with hydroxylamine to form the oxime

LXXII

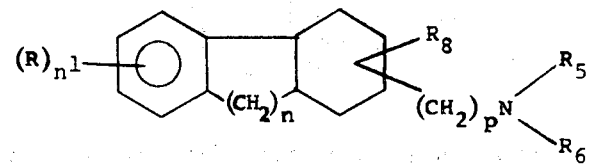

and reducing the oxime to the corresponding amine

LXXIII 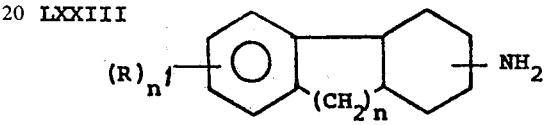

The above amine can be converted to $R_5R_6$-substituted amines employing conventional techniques.

Compounds of the structure

LXXIV

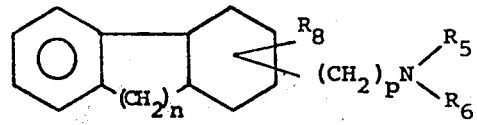

wherein the $R_8$ and the aminoalkyl group are attached to the same carbon atom can be prepared employing as the starting material compounds of the structure LXXV 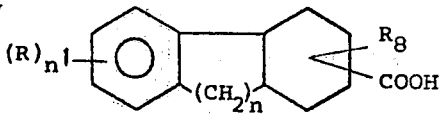

and the procedures set out hereinbefore for preparing compounds of structures LVII and LXI.

Compounds of the structure

LXXVI 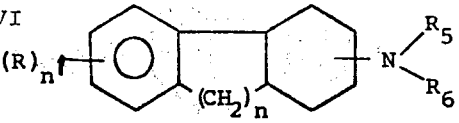

where *n* is 2 are prepared by reacting an acid of the structure

LXXVII 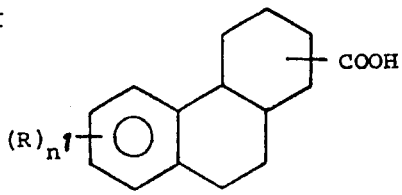 COOH with a mineral acid, such as sulfuric acid, and sodium azide to form the corresponding amine LXXVIII 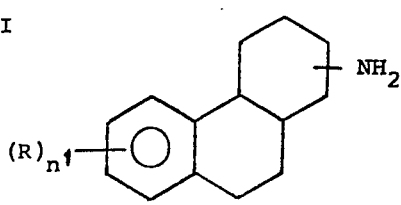 NH$_2$ The amine can be converted to a $R_5,R_6$-substituted amine employing conventional procedures.

Compounds of the structure

LXXIX 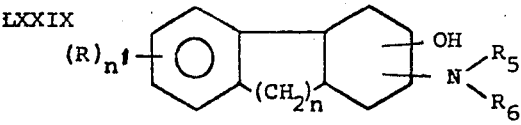

can be prepared by reacting a tetrahydro-fluorene with an oxidizing agent, such as m-chloroperbenzoic acid to form an epoxide of the structure LXXX 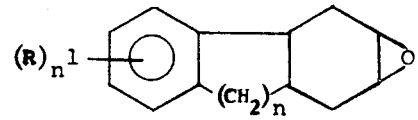

which is reacted with an amine

to form the above compound LXXIX.

Examples of aromatic starting materials of the structure:

LV 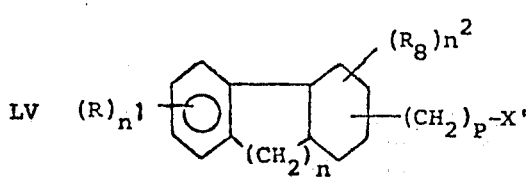

can be seen from Table C, wherein n, p and X' in the above formula are defined.

Table C

| | | |
|---|---|---|
| a) p=1, X'=Cl | n=1 |
| b) p=2, X'=Br | n=1 |
| c) p=2, X'=I | n=2 |
| d) p=4, X'=p—CH$_3$C$_6$H$_4$SO$_2$O— | n=1 |
| e) p=5, X'=Cl | n=1 |
| f) p=6, X'=Br | n=2 |
| g) p=7, X'=Cl | n=2 |
| h) p=8, X'=I | n=1 |

Examples of starting materials of the structure:

XXVII  HN<$R_5$/$R_6$ can be seen from Table D wherein $R_5$ and $R_6$ are defined.

Table D

| | $R_5$ | $R_6$ |
|---|---|---|
| a) | C$_4$H$_9$ | H |
| b) | CH$_3$— | C$_2$H$_5$ |
| c) | H | CH$_3$ |
| d) |  | H |
| e) | (S) | (S) |
| f) | (S)—CH$_2$— | (S)—CH$_2$— |
| g) | CH$_3$ | CH$_3$ |
| h) | C$_2$H$_5$ | C$_2$H$_5$ |
| i) | $R_5$ and $R_6$ together with HN is HN NH | |
| j) | $R_5$ and $R_6$ together with HN is HN O | |

Examples of starting materials of the structure:

XXVI  X'—(CH$_2$)$_p$N<$R_5$/$R_6$ can be seen from Table E wherein X', p, $R_5$ and $R_6$ are defined.

Table E

| | X' | p | $R_5$ | $R_6$ |
|---|---|---|---|---|
| a) | Br | 2 | C$_2$H$_5$ | CH$_3$ |
| b) | Br | 3 | C$_4$H$_9$ | C$_4$H$_9$ |
| c) | I | 1 | (S)—CH$_2$— | (S)—CH$_2$— |
| d) | Cl | 1 | HO—CH$_2$CH$_2$— | HOCH$_2$CH$_2$— |
| e) | I | 1 | (S) | (S) |

EXAMPLE 1

2,3-trans-4a,9a-trans-Dodecahydro-7-(hydroxymethyl)-8-(piperidinomethyl)-fluorene-2,3,4a,9a-tetrol, pentaacetate ester.

A. 10, 10A-Dihydro-4H-fluorene1,2-c]furan-1,3-(3aH, H-fluorene[bH)-dione

A solution of 1.6 g (0.01 mole) of 1-vinyl-1-indanol and 1.1 g (0.011 mole) of maleic anhydride in 5 ml of acetic anhydride is refluxed for 1 hour, cooled to 0° and filtered to give 1.43 g (60%) of the above-entitled anhydride. Several recrystallizations from ethyl acetate give needles, m.p. 186.6°–187.5°.

Anal. Calcd. for $C_{15}H_{12}O$: C,74.99; H,5.03. Found: C,74.91; H,5.12.

B. 1,2,3,9a-Tetrahydrofluorene-1,2-dicarboxylic acid, 2-methyl ester

A slurry of 10.0 g (0.0416 mole) of powdered anhydride from part A in 350 ml of methanol is refluxed for 22 hours, filtered to remove a small amount of solid and cooled to give 8.2 g of the above acid. Several recrystallizations from ethyl acetate give material of m.p. 185°–189° dec.

Anal. Calcd. for $C_{16}H_{16}O_4$: C,70.57; H,5.92. Found: C,70.44; H,6.09.

C. 1,2,3,4-Tetrahydro-1-(piperidinocarbonyl)-fluorene2-carboxylic acid, methyl ester A slurry of 5.54 g (0.02 mole) of the above acid (B) in 40 ml of benzene is heated at 50° (bath temperature) for 1 hour with 2.0 ml (ca. 3.0 g, 0.024 mole) of oxalyl chloride. After a further hour at the ambient temperature the solvent is removed in vacuo and the residue is dissolved in 50 ml of benzene and evaporated. After repeating this twice, the residue is evacuated at 0.2 mm for 30 minutes, dissolved in 40 ml of benzene and cooled in an ice bath as a solution of 5.0 ml (ca 4.3 g, 0.05 mole) of piperidine in 10 ml of benzene is added. After 2 hours the solution is partitioned between ether and 10% hydrochloric acid. The organic phase is washed with water, 10% bicarbonate, dried and evaporated to give 6.9 g of oil. Trituration with ether gives 4.8 g of solid which is recrystallized three times from hexane/benzene to give 1.64 g, m.p. 155°–156°.

Anal. Calcd. for $C_{22}H_{25}NO_3$: C,74.51; H,7.42; N,4.13. Found: C,74.22; H,7.30; N,4.09.

D. 1,2,3,4-Tetrahydro-1-(piperidinomethyl)fluoroene2-methanol, hydrochloride

A solution of 12.8 g (0.0378 mole) of the acid from part C in 350 ml of tetrahydrofuran is added over 15 minutes to a slurry of 6.6 g (0.174 mole) of lithium aluminum hydride in 250 ml of ether. The mixture is heated at reflux for 3 hours, cooled to 0° and 25 ml of sat. potassium carbonate solution is added. The mixture is filtered and the filtrate dried and evaporated in vacuo to yield 12.87 g of viscous liquid. This is converted to the hydrochloride by reacting it with hydrochloric acid in the presence of isopropanol and ether and the hydrochloride is recrystallized once from ethanol-methanol and three times from methanol to yield 1.7 g (0.00512 mole) 13.5%) of crystalline solid which decomposes above 242°. A small sample is converted to the free base, and thin layer chromatography on this sample shows a single spot. All filtrates are combined and concentrated to yield 4.5 g of the above titled compound in the form of a solid.

E. 1,2,3,4,4a,5,8,9a-Octahydro-1-(piperidinomethyl)fluorene-2-methanol

A solution of 16.3 g of crude 1,2,3,4-tetrahydro-1-(piperidinomethyl)fluorene-2-methanol, in the form of the free base, dissolved in 300 ml of ether is added to 1.5 liter of liquid ammonia. An amount of 8.4 g (1.2 moles) of lithium ribbon is added over 1.5 hr. and then 150 ml of abs. ethanol added over 60 minutes; the ammonia is evaporated and the residue cooled and partitioned between 400 ml of water and 300 ml of ether. The aqueous layer is washed with 2 × 250 ml of ether, and then the extracts are combined, washed with sat. sodium chloride solution, dried, and evaporated in vacuo to give 13.1 g (0.0434 moles) of the above titled compound.

F. 2.3-trans-4a,9a-trans-Dodecahydro-7-(hydroxymethyl)-8-(piperidinomethyl)-2,3,4a,9a-tetrol A solution of 12.9 g (0.043 mole) of crude diene from part E in 90 ml of cold 98% formic acid is warmed to 20°, and 11.3 ml of 30% hydrogen peroxide is added dropwise. The temperature rises to 45° during the addition, and a room temperature water bath is used to prevent further rise. The mixture is stirred at room temperature overnight, and then diluted with water and evaporated in vacuo three times. The residue is dissolved in 95% ethanol, 30 g of potassium hydroxide in 80 ml of water added and the mixture stirred at reflux under $N_2$ for 90 minutes. The mixture is cooled, concentrated in vacuo, and then extracted with 5 × 250 ml of ether. The ether extracts are combined, washed with sat. sodium chloride solution, dried and evaporated in vacuo to give 7.5 g of a foam; an additional 1.7 g of foam is obtained by extracting the aqueous layer with 750 ml of ethyl acetate. The 7.5 g of foam is dissolved in methanol and cooled overnight to give 0.6 g (0.0016 mole) 3.72% of solid identified as the title compound.

G. 2,3-trans-4a,9a-trans-Dodecahydro-7-(hydroxymethyl)-8-(piperidinomethyl)fluorene-2,3,4a,9a-tetrol, pentaacetate ester A solution of 0.55 g (0.00149 mole) of pentol, from part F, in 30 ml of acetic anhydride and 1 ml of glacial acetic acid is cooled in dry ice-acetone bath, 1 ml of 70% perchloric acid added and the mixture stored at −15° overnight. The mixture is partitioned between 100 ml of ether and 100 ml of cold conc. ammonium hydroxide. The aqueous layer is washed with 3 × 200 ml of ether, and then all ether extracts are combined, washed with sat. sodium chloride solution, dried and evaporated in vacuo to give 0.9 g of crude product.

This is recrystallized from hexane ethyl acetate to give 0.477 g (0.000825 mole) of white solid (55%), identified as the title product m.p. 188.5°–191°.

Anal. Calcd. for $C_{30}H_{45}NO_{10}$: C,62.10; H,7.83; N,2.42. Found: C,62.13; H,7.53; N,2.28.

EXAMPLE 2

1,2,3,9a-Tetrahydro-2-(piperidinomethyl)-fluorene-1-methanol, hydrochloride

A. 1,2,3,9a-Tetrahydro-2-(piperidinocarbonyl)fluorene-1-carboxylic acid

A solution of 10.0 g (.041 mole) of 10,10A-dihydro-4H-fluorene[1,2-c]furan-1,3-(3aH,10bH)dione and 7.8 g (.092 mole) of piperidine in 250 ml of acetonitrile is left standing at room temperature for 24 hours. The solution is filtered to give 13.6 g of solid. The filtrate is evaporated in vacuo to give 5 g of mixed solid and oil product. The solids are combined, dissolved in ether, washed with 5% hydrochloric acid, water, and sat. sodium chloride solution. The ether is dried and evaporated in vacuo to give 15.6 g of foam which is recrystallized from ethyl acetate to give 10.5 g of white solid identified as the title compound, m.p. 161–167.

B. 1,2,3,9a-Tetrahydro-2-(piperidinomethyl)fluorene-1-methanol, hydrochloride

A solution of 6.32 g (0.019 mole) of the acid from part A in 200 ml of warm tetrahydrofuran and 50 ml of dioxane is added over 45 min. to a slurry of 3.53 g (.093 mole) of lithium aluminum hydride in 150 ml of ether. The mixture is stirred at reflux for 4 hours and overnight at room temperature. The mixture is cooled to 0°, and 25 ml of sat. potassium carbonate solution added. The solution is filtered and evaporated in vacuo to give 6.46 g of crude oil. This is converted to the hydrochloride salt and recrystallized six times from isopropanol-methanol to give a white solid identified as the title compound, 1.08 g (16.6%), with double m.p. 208°–210° and 239°–245°.

Anal. Calcd. for $C_{20}H_{27}OH.HCL$: C,71.94; H,8.45; N,4.19; Cl,10.6; O,4.79. Found: C,71.97; H,8.55; N,4.29; Cl,10.7.

EXAMPLE 3

2,3-trans-4a,9a-trans-Dodecahydro-8-(hydroxymethyl)-7-(piperidinomethyl)-fluorene-2,3,4a,9a-tetrol, pentaacetate ester A. 1,2,3,4-Tetrahydro-2-(piperidinocarbonyl)-fluorene1-carboxylic acid A solution of 20 g (0.083 mole) of 10,10A-dihydro-4H-fluorene[1,2-c]furan-1,3-(3aH,10bH)-dione and 15.5 g (0.182 mole) of piperidine in 700 ml of acetonitrile is left standing at room temperature overnight. The solution is then evaporated to dryness in vacuo, dissolved in chloroform, washed with 5% hydrochloric acid solution and sat. sodium chloride solution, dried and evaporated in vacuo to give 32.8 g of foam. The foam is recrystallized from ethyl acetate to give a white solid, 22.9 g (0.0706 mole) identified as the title compound.

B. 1,2,3,4-Tetrahydro-2-(piperidinomethyl)-fluorene-1-methanol, hydrochloride

A solution of 25.37 g (0.0782 mole) of the carboxylic acid from part A in tetrahydrofuran is reduced with lithium aluminum hydride to give 17.7 g of oil. The hydrochloride salt is prepared by reacting the oil with hydrochloric acid in the presence of isopropanol and ether. The hydrochloride salt is collected and recrystallized from isopropanol-methanol to give 7.2 g of solid (27.6%). A second recrystallization on 3 g of this solid gives a white solid 2.1 g, identified as the title compound, m.p. 239°–240°.

Anal. Calcd. for $C_{20}H_{27}NO.HCl$: C,17.94; H,8.45; N,4.19; Cl,10.61. Found: C,17.93; H,8.40; N,4.16; Cl,10.84.

C. 1,2,3,4,4a,5,8,9a-Octahydro-2-(piperidinomethyl)-fluorene-1-methanol

A water solution of 18.78 g (0.0554 mole) of a mixture of 1,2,3,9a-tetrahydro-2-(piperidinomethyl)fluorene-1-methanol, hydrochloride and 1,2,3,4-tetrahydro-2-(piperidinomethyl)fluorene-1-methanol, hydrochloride is basified, extracted with 3 × 300 ml of chloroform and the extracts washed with sat. sodium chloride solution, dried over sodium sulfate and magnesium sulfate and evaporated in vacuo to give 18.4 g of liquid. This is dissolved in 200 ml of ether and added to 1.5 liters of liquid ammonia. An amount of 11.5 g (1.64 g-atoms) of lithium ribbon is added over 75 min., 150 ml of ether is added and the mixture stirred at reflux for 90 min. An amount of 15 ml of abs. ethanol is added over 60 min. the ammonia evaporated, and the residue cooled to 0° and partitioned between 500 ml of ether and 400 ml of water. The aqueous layer is washed with 2 × 300 ml of ether and than all ether extracts are combined, washed with sat. sodium chloride solution, dried and evaporated in vacuo to give 16.97 g of oil, identified as the title compound.

D. 2.3-trans-4a,9a-trans-Dodecahydro-8-(hydroxymethyl)-7-(piperidinomethyl)fluorene-2,3,4a,9a-tetrol A solution of 16.97 g (0.056 mole) of diene from part C in 100 ml of 98% formic acid prepared at 5°, is warmed to 15° and 15 ml of 30% hydrogen peroxide is added over 15 minutes causing the temperature to rise to 27°. The mixture is stirred for 2.5 hours at 30°, warmed to 43° for 45 minutes, and stirred overnight at room temperature. The mixture is diluted with 150 ml of water and evaporated in vacuo three times to give a yellow oil. The oil is dissolved in 100 ml of 95% ethanol and 24 g (0.43 mole) of potassium hydroxide in 50 ml of water and the mixture stirred at reflux for 1 hour. The mixture is cooled and extracted with 4 × 250 ml of ether to give 2.3 g (0.006 mole, 11.05%) of solid and 8.1 g of foam. The solid is recrystallized from ethyl acetate-methanol to give 1.3 g of solid, identified as the title compound.

E. 2,3-trans-4a,9a-trans-Dodecahydro-8-(hydroxymethyl)-7-(piperidinomethyl)-fluorene-2,3,4a,9a-tetrol, pentaacetate ester A suspension of 1.3 g (0.0035 mole) of pentol from part D in 40 ml of acetic anhydride and 1.5 ml of glacial acetic acid is cooled in dry-ice acetone bath, and 1.3 ml of 70% perchloric acid added. The mixture is stored overnight at −15°, and then maintained at −15° while 25 ml of methanol is added dropwise. The mixture is poured into 100 ml of cold conc. ammonium hydroxide and extracted with 3 × 200 ml of ether. The ether is washed with sat. sodium chloride solution, dried and evaporated in vacuo to give 2.1 g of foam (100% crude). This is recrystallized twice from hexane-ethyl acetate to give 0.59 g of white solid identified as the title product, m.p. 160°–210°.

Anal. Calcd. for $C_{30}H_{45}NO_{10}$: C,62.16; H,7.83; N,2.42. Found: C,62.03; H, 7.55; N,, 2.23.

EXAMPLE 4

1,2,3,4-Tetrahydro-1-[[2-(hydroxymethyl)-piperidino]methyl]fluorene-2-methanol

A. 2-Carbomethoxy piperidine

A slurry of 26 g (0.20 mole) of pipecolinic acid in 100 ml of methanol is cooled to −10° and 16.7 ml (0.22 mole) of thionyl chloride added over 5 minutes. The slurry is allowed to warm to ambient temperature and stirred overnight whereupon a thick slurry forms. Addition of 300 ml of methanol gives a solution which is evaporated in vacuo. The residue is suspended in 100 ml in methanol, treated with a solution of 10.8 g (0.2 mole) of sodium methoxide in 100 ml of methanol, and diluted with 400 ml of ether. The solid which forms is filtered and the filtrate evaporated and redissolved in ether. Filtration, evaporation and solution are repeated three times and the final residue distilled in vacuo to give 24.6 g (85%) of the above titled ester, bp. 70°–70.5° at 4.0 mm.

B. 1,2,3,4-Tetrahydro-1-(chlorocarbonyl)-fluorene-2-carboxylic acid, methyl ester 1,2,3,4-Tetrahydro-1-(piperidinocarbonyl)fluorene-2-carboxylic acid, methyl ester, 20 g. (0.073 mole) is reacted with oxalyl chloride in the benzene to form the title acid chloride.

C. 1-[(2-Carboxypiperidino)carbonyl]-1,2,3,4-tetrahydrofluorene-2-carboxylic acid, dimethyl ester The acid chloride from part B is dissolved in 200 ml of benzene and treated with a solution of 12.2 g (0.087 mole) of 2-carbomethyoxypiperidine and 10.1 g (0.10 mole) of triethyl amine in 70 ml of benzene. After stirring overnight at ambient temperature the slurry is poured into 200 ml each of ether and 5% hydrochloric acid. The organic layer is washed with water, sat'd salt solution, dried and evaporated to give 31.7 g of oil which slowly crystallizes from ether at −15° to give 23.4 g of the title compound. Recrystallization of 3.0 g of this material twice from hexane/ethyl acetate gives 1.84 g, m.p. 141°–143°.

Anal. Calcd. for $C_{23}H_{27}NO_5$: C,69.50; H,6.85; N,3.52. Found: C,69.23; H,7.11; N,3.51.

D. 1,2,3,4-Tetrahydro-1-[[2-(hydroxymethyl)-piperidino]methyl]fluorene-2-methanol A solution of 4.0 g (0.01 mole) of the compound from part C in 30 ml of tetrahydrofuran is added to a slurry of 1.2 g (0.03 mole) of lithium aluminum hydride in 50 ml of ether. After refluxing for 6 hours, the mixture is cooled, the excess hydride destroyed with sat'd potassium carbonate solution and the salts filtered and washed well with ether and chloroform. The residue is evaporated to give 2.94 g of solid. Two recrystallizations from ether gives 1.34 g, of the above titled product, m.p. 151–159°.

Anal. Calcd. for $C_{21}H_{29}NO_2$: C,77.02; H,8.93; N,4.28. Found: C,77.19; H,8.89; N,4.29.

EXAMPLE 5

2,3-trans-4a,9a-trans-Dodecahydro-6-(1-pyrrolidinyl)fluorene-2,3,4a,9a-tetrol

A. 1-(1,2,3,9a-Tetrahydrofluoren-3-yl)pyrrolidine, hydrochloride

A solution of 39 g (0.3 mole) of 1-indanone and 50 ml (excess) of pyrrolidine is refluxed in 250 ml of benzene with ca. 100 mg of TsOH under nitrogen. Over 4 hours, 8 ml of water is collected. The benzene and excess pyrrolidine are removed in vacuo and the crude enamine refluxed for 17 hours under nitrogen with 23 g (0.33 mole) of freshly distilled methyl vinyl ketone in 350 ml of benzene. The solvent is removed in vacuo and the residue dissolved in 400 ml of methanol and 20 g (0.5 mole) of sodium borohydride added at 25°–35° over 30 minutes. After 2 hours, 10% hydrochloric acid is added to pH 1 and the methanol removed in vacuo. The aqueous solution is extracted with ether (2 × 200 ml. discard), basified with 10% sodium hydroxide and extracted with ether (2 × 300 ml). Drying and solvent removal gives 54.6 g of oil which is converted to the hydrochloride in ether. Recrystallization from methanol gives, in 2 crops, 24.6 g (30%) of yellow solid, essentially homogeneous on thin layer chromatography.

A portion is recrystallized twice from methanol to give 1.7 g, m.p. >270°.

Anal. Calcd. for $C_{17}H_{22}NCl$: C,74.04; H,8.03; N,5.07; Cl,12.85. Found: C,74.20; H,8.14; N,5.18; Cl,12.56.

The assignment of the double bond in this position is based on the nmr of the free base (the hydrochloride is too insoluble) and the uv spectrum.

B. 2,3-trans-4a,9a-trans-Dodecahydro-6-(1-pyrrolidinyl)-fluorene-2,3,4a,9a-tetrol. (Isomer A)

A solution of the free base from 21.6 g of 1-(1,2,3,9a-tetrahydrofluoren-3-yl)pyrrolidine in 200 ml of ether is added to 1.5 liters of liquid ammonia. Over 30 minutes, 16.2 g (2.34 g-atom) of lithium is added followed by 180 ml of ethanol over 150 minutes. The ammonia is evaporated and the residue processed as usual to give 18.4 g of oil with negligible absorption at >230 m$\mu$(3.3 × $10^{-3}$ molar).

This material is dissolved in 180 ml of cold formic acid, warmed to 20° and 20 ml of 30% hydrogen peroxide added over 5 minutes. The temperature rises to 28° (20° water bath) over 20 minutes. After stirring overnight the solution is diluted with 250 ml of water and the solvent removed in vacuo. The residue is refluxed for 1 hour under nitrogen with 30 g of sodium hydroxide in 150 ml each of water and ethanol. This solution is cooled, diluted with 500 ml of water and extracted with ether (5 × 200 ml). Drying and solvent removal gives 20.1 g of solid which is dissolved in a boiling mixture of 600 ml of 2:1 ethyl acetate-methanol. Cooling gives 3.64 g, essentially homogeneous on TLC $R_f$=ca. 0.15 (alumina, 10% methanol/chloroform).

The mother liquor is evaporated to dryness, triturated with 100 ml of boiling ethyl acetate, cooled and filtered to give 6.4 g, mainly one spot with $R_f$=ca. 0.30 (alumina, 10% methanol/chloroform). Two recrystallizations from ethyl acetatemethanol (cooled to room temperature) gives 2.1 g of the title compound m.p. 233°–236°, homogeneous on TLC.

Anal. Calcd. for $C_{17}H_{29}NO_4$: C,65.65; H,9.39; N,4.50. Found: C,65.49; H,9.33; N,4.44.

EXAMPLE 6

2,3-trans-4a,9a-trans-Dodecahydro-6-(1-pyrrolidinyl)fluorene-2,3,4a,9a-tetrol, tetraacetate ester (Isomer A)

A slurry of 1,9 g of 2,3-trans-4a,9a-trans-dodecahydro-6-(1-pyrrolidinyl)fluorene-2,3,4a,9a-tetrol (prepared as in Example 5) in 300 ml of acetic anhydride is cooled to −78° and 1.0 ml of 70% perchloric acid added. After standing overnight at −10°, 30 ml of methanol is added (<−10°). The resulting solution is poured into a mixture of ice and 100 ml of ammonium hydroxide and extracted with ether. Drying and solvent removal gives 2.64 g of oil which solidifies on trituration with hexane. Two recrystallizations from hexane/ethyl acetate gives 1.52 g of the title product, m.p. 179.5°–181.5°.

Anal. Calcd. for $C_{25}H_{37}NO_8$: C,62.61; H,7.78; N,2.92. Found: C,62.39; H,7.85; N,2.76.

EXAMPLE 7

A. 1-(1,2,3,4-Tetrahydrofluoren-2-yl)pyrrolidine, hydrochloride

A solution of 40 g (0.3 mole) of 2-indanone, 100 mg of TsOH and 50 ml pyrrolidine in 300 ml of benzene is refluxed with a Dean-Stark trap for 3 hours (8.9 ml of water is collected). The solvent and excess amine are removed in vacuo and the residue refluxed overnight in 300 ml of benzene with 20 g (0.29 mole) of methyl vinyl ketone. The solvent is removed in vacuo and the solid residue slurried with 500 ml of methanol. Over 10 minutes, 20 g of sodium borohydride is added at 30°–35°. The solution is stirred at room temperature for 3 hours, cooled to 0° and 10% hydrochloric acid added to pH =1. The solution is diluted with water 1.2 liters and the methanol removed in vacuo. Cooling gives a solid which is filtered and dried (33.6 g). Two recrystallizations of 3.6 g of this material from ethanol give 2.06 g of the title compound A, m.p. 273°–275° dec.

Anal. Calcd. for $C_{17}H_{21}N \cdot HCl$:
C,74.04: H,8.043; N,5.07; Cl,12.85.
Found: C, 74.02; H,8.14; N,5.03; Cl,12.99.

B. The base material, i.e. 1-(1,2,3,4-tetrahydrofluoren-2-yl)pyrrolidine can be converted to the corresponding tetrol and the tetrol to the tetraester employing the procedures of Examples 5 and 6.

EXAMPLE 8

2,3-trans-4-a,9a-trans-Dodecahydro-6-(1-pyrrolidinyl)fluorene2,3,4a,9a-tetrol. (Isomer B)

The 3.64 g first crop described in the preparation of 2,3-trans-4a,9a-trans-dodecahydro-6-(1-pyrrolidinyl)-fluorene-2,3,4a,9a-tetrol is recrystallized twice from methanol to give 1.3 g, m.p. 269°–275° dec., homogeneous on TLC.

Anal. Calcd, for $C_{17}H_{29}NO_4$: C,65.56; H,9.39; N,4.50.
Found: C,65.39; H,9.23; N,4.32.

From the mother liquor a further 1.7 g of TLC pure material is obtained in two crops.

EXAMPLE 9

2,3-trans-4a,9a-trans-Dodecahydro-6-(1-pyrrolidinyl)fluorene-2,3,4a,9a-tetrol, tetraacetate ester. (Isomer B).

A slurry of 1.7 g of 2,3-trans-dodecahydro-6-(1-pyrrolidinyl)fluorene-2,3,4a,9a-tetrol in 30 ml of acetic anhydride is cooled to −78° And 1.0 ml of 70% perchloric acid added. After standing overnight at −10°, 30 ml of methanol is added (<−10°). The resulting solution is poured onto a mixture of ice and 100 ml of ammonium hydroxide and extracted with ether. Drying and solvent removal gives 2.39 g of oil which quickly solidifies. Two recrystallizations from hexane/-ethyl acetate gives 1.15 g of the title compound, m.p. 157°–159.5°.

Anal. Calcd. for $C_{25}H_{37}NO_8$: C,62.61; H,7.78; N,2.92. Found: C,62.84; H,7.98; N,2.89.

EXAMPLE 10

2,3-trans-4a,9a-trans-Dodecahydro-7-(1-pyrrolidinyl)-fluorene-2,3,4a,9a-tetrol. (Isomer A)

A. 1-(1,2,3,4,4a,5,8,9a-Octahydrofluoren-2-yl)pyrrolidine

A solution of 20.1 g (0.084 moles) of 1-(1,2,3,4-tetrahydrofluoren-2-yl)pyrrolidine, prepared as per Example 7, in 400 ml of tetrahydrofuran and 100 ml of ether is added to 2.5 l of liquid ammonia. 12.25 g (1.72 g-atoms) of lithium ribbon is added over 25 min and the mixture stirred for 15 minutes. 160 ml of ethanol is added over 2.5 hr., the ammonia evaporated and the residue added to 1 liter of cold water. The layers are separated and the aqueous layer is extracted with ether (2 × 300 ml). The combined ether layers are washed, dried and evaporated in vacuo to give 20.2 g of oil of the above title.

B. 2,3-trans-4a,9a-trans-Dodecahydro-7-(1-pyrrolidinyl)-fluorene-2,3,4a,9a-tetrol An amount of 21 ml of 30% hydrogen peroxide is added over 15 minutes to a solution of 20.1 g (0.083 moles) of diene from part A in 200 ml of 97–100% formic acid. The temperature rises from 24° to 32° during addition and a room temperature water bath is used to prevent further increase. The mixture is stirred overnight at room temperature. The mixture is diluted with water and evaporated in vacuo twice to give a dense liquid. This liquid is stirred at reflux for 1 hour under nitrogen in a solution of 150 ml of ethanol, 16 g of potassium hydroxide, and 75 ml of water. Extraction of the aqueous solution with ether (800 ml) and 5% methanol in chloroform (900 ml) gives a total of 20.4 g of crude material on evaporation. Crystallization from ethyl acetate-methanol gives 5 g of solid, isomer A, m.p. 189°–199°. The 5 g of isomer A is recrystallized twice from ethyl acetate-methanol to give 1.7 g of solid. An amount of ca. 0.1 g of pale yellow crystals, m.p. 262°–263° are removed by hand to leave the white crystalline product, of the above title, 1.57 g, m.p. 213°–217° (6.1%). A second crop gives 0.71 g, m.p. 209°–215°.

Anal. Calcd. for $C_{17}H_{29}NO_4$: 311.4 g/mole C,65.56; H,9.39; N,4.50 Found: C,65.51; H,9.54; N,4.58

EXAMPLE 11

2,3-trans-4a,9a-trans-Dodecahydro-7-(1-pyrrolidinyl)-fluorene-2,3,4a,9A-tetrol, tetraacetate ester A solution of 1.13 g (0.0036 mole) of 2,3-trans-4a,-9a-trans-dodecahydro-7-(1-pyrrolidinyl)-fluorene-2,3a,4a,9a-tetrol in 40 ml of acetic anhydride and 3 ml of glacial acetic acid is cooled in a dry ice-acetone bath while 1.5 ml of 70% perchloric acid is added. The mixture is stored overnight below 0°. The solution is cooled to −15° while 30 ml of methanol is added and then partitioned between 100 ml each of cold conc. ammonium hydroxide and ether. The aqueous layer is extracted with ether (2 × 100 ml) and the combined extracts are washed with saturated sodium chloride solution, dried, and evaporated in vacuo to give 1.51 g of pale yellow solid (87% crude). Recrystallization from hexane-ethyl acetate gives 0.9 g, m.p. 187°–195°, 52.4%.

Anal. Calcd. for $C_{25}H_{37}NO_8$: 479.5 g/mole C, 62.61; H, 7.78; N, 2.92 Found: C, 62.46; H, 8.02;N, 2.97

EXAMPLE 12

2,3-trans-4a,9a-trans-Dodecahydro-8-(dimethylaminomethyl)-fluorene-2,3,4a,9a-tetrol A. 1,2,3,4,4a,9a-Hexahydrofluorene-1-carboxylic acid A solution of 21.0 g (0.10 mole) of fluorene-1-carboxylic acid in 25 ml of absolute ethanol is added to 500 ml of liquid ammonia and the solution treated portionwise with 4.2 g (0.60 mole) of lithium cut in small pieces. After evaporation of the $NH_3$, the residue is cooled in ice and treated first with water and then with sufficient conc. HCl to render it strongly acidic. The crude partially reduced product is filtered off and dissolved in acetic acid. Reduction of the solution over 1 g of $PtO_2$ under up to 55 psi of $H_2$ is complete after about 1 equivalent of $H_2$ is taken up. The solution is freed of catalyst and taken to dryness. Recrystallization from hexane affords the desired product, mp 138°–139°.

B. 1-Dimethylaminomethyl-1,2,3,4,4a,9a-hexahydrofluorene

To 10.8 g (0.05 mole) of the acid is added 50 ml (XS) thionyl chloride and the solution heated on the steam bath for 2 hrs. Excess reagent is removed on the water aspirator and then benzene added and removed twice. The residual acid chloride is taken up in 50 ml of benzene and added with cooling and stirring to a solution of 10 g. (XS) of dimethylamine in 50 ml of benzene. Stirring is continued for several hours, the precipitated salt filtered off and the filtrate washed with water. Concentration of the dried organic filtrate leaves 12.2 g crude amide. The amide is dissolved in 50 ml of dioxane and added dropwise to a suspension of 5 g of lithium aluminum hydride in 100 ml of ether. After several hours at reflux, the mixture is decomposed with saturated $K_2CO_3$ and filtered. Concentration of the filtrates leave 10.5 g of the title compound.

C. 1-Dimethylaminomethyl-1,2,3,4,5,8,4a,9a-octahydrofluorene

The 1-dimethylaminomethyl-1,2,3,4,1a,4a-hexahydrofluorene of part B is then subjected to a Birch reduction as per Example 1, part E, to form the title compound.

D. 2,3-trans-4a,9a-trans-Dodecahydro-8-(dimethylaminomethyl)-fluorene-2,3,4a,9a-tetrol The diene compound prepared in part C is then reacted with hydrogen peroxide in the presence of formic acid as per Example 1, part F, to form the title tetrol compound.

EXAMPLE 13

2,3-trans-4a,9a-trans-Dodecahydro-9-(dimethylaminoethyl)-fluorene-2,3,4a,9a

A solution of 43.2 g (0.20 mole) of 1,2,3,4,4a,9a-hexahydrofluorene-4-carboxylic acid (prepared from fluorene-4-carboxylic acid as per the procedure of Example 12A) in 250 ml of dioxane is added dropwise to a suspension of 25 g of lithium aluminum hydride in 1 l. of ether and the mixture stirred under reflux for 3 hrs. After decomposition with saturated potassium carbonate solution, the mixture is filtered, and solvent removed from the filtrate leaving a quantitative yield of 1,2,3,4,4a,9a-hexahydrofluorenyl-4-carbinol.

The above alcohol is taken up in 200 ml of $CHCl_3$, treated with a few ml of pyridine, cooled in an ice bath and stirred while 20 g of phosphorus tribromide is added dropwise. After stirring for several hours cold, the mixture is poured onto ice water, the layers separated, and the organic layer dried over magnesium sulfate and freed of solvent, leaving the desired, 1,2,3,4,4a,9a-hexahydro-4-fluorenylmethyl bromide.

The above bromide is dissolved in 500 ml of solvent, consisting of 20% t-butanol and 80% N-methyl-2-pyrrolidine, and treated with 25 g of KCN. The stirred mixture is heated on the steam bath for 6 hrs, cooled and poured into water. The product is extracted into ether and the aqueous portion reextracted several times. The combined organic extracts are washed with water, dried and taken to dryness, ultimately on the oil pump, leaving about 30 g of desired 1,2,3,4,4a,9a-hexahydro-4-fluorenylacetonitrile as an oil.

The above nitrile is dissolved in 100 ml of ether and added to a suspension of 15 g of LAH in 500 ml of ether dropwise over 15 min. After 3 hrs at reflux, the mixture is decomposed with sat'd $K_2CO_3$ and filtered. Solvent removal from the filtrate leaves 28 g of oily 2'-[1,2,3,4,4a,9a-tetrahydro-4-fluorenyl]-ethylamine.

The above amine is treated with 25 ml of 37% formalin in the cold, followed by 35 ml of 88% formic acid with swirling. The solution is then heated on the steam bath overnight, then taken to dryness in vacuum. The residue is dissolved in water, rendered strongly basic with 50% caustic and extracted with ether. Removal of solvent from the dried extracts leaves about 30 g of oil N,N-dimethyl-2'-[1,2,3,4,4a,9a-hexahydrofluorenyl]-ethylamine.

This is then subjected to a Birch reduction as per Example 1 E to give N,N-dimethyl[-1,2,3,4,5,8,4a,9a-octahydro-4-fluroenyl]-2'-ethylamine; which is reacted with hydrogen peroxide in the presence of formic acid as per Example 1F to form the title compound.

EXAMPLE 14

2,3-trans-4a,9a-trans-Dodecahydro-8-(dimethylaminopropyl)-fluorene-2,3,4a,9a-tetrol To a solution of 0.5 mole of dimethylaminopropyl magnesium chloride freshly prepared in 500 ml of THF is added dropwise a solution of 9.3 g (0.05 mole) of 1,2,3,4,4a,9a-hexahydro-fluoren-3-one with ice cooling. The mixture is then heated under reflux for 2 hrs, cooled and decomposed with saturated $NH_4Cl$ solution. The separated organic layer is dried over $MgSO_4$ and freed of solvent, leaving about 13g of crude 3,3'-dimethylaminopropyl-3-hydroxy-1,2,3,4,4a,9a-hexahydrofluorene.

The above alcohol is treated cautiously with 50 ml of thionyl chloride then heated on the steam bath for 2 hrs. Excess reagent is removed at the water aspirator and the residue is dissolved in water and rendered strongly basic with caustic. The mixture of olefin is extracted into ether, dried and taken to dryness. The residue is taken up in 75 ml of glacial acetic acid, treated with 1 g of $PtO_2$, and reduced under up to 55 psi of $H_2$ on a Parr apparatus until uptake ceases. After filtration and solvent removal the desired N,N-dimethyl-3'-[1,2,3,4,4a,9a-hexahydro-3-fluorenyl]propylamine is obtained, on basification, as an oil.

Birch reduction of the oil in accordance with Example 1E provides N,N-dimethyl-3'-[1,2,3,4,5,8,4a,9a-octahydro-3-fluorenyl]propylamine, which is reacted with hydrogen peroxide in the presence of formic acid as per Example 1F to form the title compound.

EXAMPLE 15

2,3-trans-4a,9a-trans-Dodecahydro-5-(diethylamino)fluorene-2,3,4a,9a-tetrol

To 18.6 g (0.10 mole) of 1,2,3,4,4a,9a-hexahydrofluoren-4-one in 75 ml of pyridine is added 20 g of hydroxylamine hydrochloride and the mixture heated under reflux for 2 hrs. The hot mixture is poured onto ice and the product extracted into $CHCl_3$, dried and freed of solvent. A quantitative yield of the oxime remains.

The above oxime is dissolved in 100 ml of dioxane and added to a suspension of 10 g of lithium aluminum hydride in 500 ml of ether. The mixture is stirred under reflux for 3 hrs, then decomposed with sat'd $K_2CO_3$ sol'n and filtered. Removal of solvent leaves about 16 g of 4-amino-1,2,3,4,4a,9a-hexahydrofluorene.

The above amine is added to a suspension of 40 g of $K_2CO_3$ in 200 ml of methyl ethyl ketone and stirred while 22 g of ethyl bromide is added slowly over 2 hrs. The mixture is then heated under reflux for 5 hrs., cooled and filtered. Solvent is removed from the filtrate and the residue mixed with water and $CHCl_3$. The organic layer is dried and freed of solvent to leave about 15 g of N,N-diethyl-4-amino-1,2,3,4,4a,9a-hexahydrofluorene which is subjected to a Birch reduction as per Example 1E to give N,N-diethyl-4-amino-1,2,3,4,5,8,4a,9a-octahydrofluorene which is reacted with hydrogen peroxide in the presence of formic acid as per Example 1 F to form the title compound.

EXAMPLE 16

2,3-trans-4a,9a-trans-Dodecahydro-8a-(dimethylaminoethyl)-fluorene-2,3,4a,9a-tetrol To 500 ml of liquid NH₃ is added a solution of 9.84 g (0.04 mole) of 9a-carboxymethyl-1,2,3,4,4a,9a-hexahydrofluoren-9-ol (JACS 82 2561 (1960)) in 100 ml of THF. The mixture is then treated portionwise with 7 g of lithium cut in small pieces followed dropwise by sufficient absolute ethanol to discharge the blue color. After NH₃ has evaporated, the cooled mixture is treated with water and carefully acidified. The desired 9a-carboxymethyl-1,2,3,4,5,8,4a,9a-octahydrofluorene is isolated by extraction with ether, drying and solvent removal.

The resulting crude acid is converted to acid chloride by dissolving the acid in CHCl₃ and treating with excess oxalyl chloride. Removal of solvent and excess reagent in vacuum leaves the intermediate acid chloride which is converted to the amide and the amine, which in turn is converted to the title tetrol compound as per the procedure of Example 12.

EXAMPLE 17

2,3-trans-4a,10a-trans-perhydro-7-amino-phenanthrene-2,3,4a,10a-tetrol

To a mixture of 11.7 g (0.05 mole) of 1,2,3,4,4a,9,10,10a-octahydrophenanthrene-2-carboxylic acid, 80 ml of conc. H₂SO₄ and 200 ml of CHCl₃ is added with stirring at 50°–60° 3.64 g of sodium azide in small portions. After completed addition, heating at 50° is continued for 1 hr longer, the the mixture poured onto ice and then rendered alkaline with caustic. The product is extracted into CHCl₃, dried and freed of solvent to give about 9 g of 2-amino-1,2,3,4,4a,-9,10,10a-octahydrophenanthrene, which is subjected to a Birch reduction as per Example 1E and then reacted with hydrogen peroxide in the presence of formic acid as per Example 1F to form the title compound.

EXAMPLE 18

2,3-trans-4a,10a-trans-perhydro-6-[3'-dimethylaminopropyl]-phenanthrene-2,3,4a,10a-tetrol To a freshly prepared soln. of 0.5 mole of dimethylamino-propylmagnesium chloride in 500 ml THF is added dropwise with cooling a solution of 19.8 g (0.10 mole) of 1,2,3,9,-10,10a-hexahydro-3-oxophenanthrene. After 2 hrs. at reflux, the mixture is cooled and decomposed with sat'd NH₄Cl solution. The separated organic layer is dried and freed of solvent ultimately on the oil pump.

The crude product is dissolved in 100 ml of glacial acetic acid, treated with 20 ml of conc. HCl, warmed briefly and then treated with 1 g of PtO₂ and subjected to reduction under 40–50 psi of H₂ until uptake ceases. After catalyst removal, the filtrate is taken to dryness and the residue dissolved in water and basified. Product is extracted into CHCl₃, dried and freed of solvent. 3-[3'-Dimethylaminopropyl]-1,2,3,4,4a,9,10,10a-octahydrophenanthrene is obtained as an oil, which is subjected to the Birch reduction procedure described in Example 1E to give 3-[3'-dimethylaminopropyl]-1,2,3,4,4a,5,8,9,10,10a-decahydrophenanthrene which is reacted with hydrogen peroxide in the presence of formic acid as per Example 1F to give the title compound.

EXAMPLE 19

2,3-trans-4a,10a-trans-perhydro-6-piperidino-phenanthrene-2,3,4a,10a-tetrol

A mixture of 19.8 g (0.10 mole) of 1,2,3,9,10,10a-hexahydro-3-oxophenanthrene and 40 g of piperidine in 300 ml of dry ether under nitrogen is treated dropwise at 0°–10°C with a solution of 10 g of titanium tetrachloride in 150 ml of benzene. After 48 hrs. at room temperature, the mixture is filtered and the filtrate taken to dryness ultimately on the oil pump. The crude product is dissolved in 100 ml of methanol and treated with 6 g of NaBH₄ in small portions. After 2 hrs. the mixture is brought to reflux for 1 hr., then cooled and diluted with water. Product is extracted into ether, dried and freed of solvent. 3-N-piperidino-1,2,3,4,9,10-hexahydrophenanthrene is obtained as an oil, which is subjected to a Birch reduction as per Example 1E to provide 3-N-piperidino-1,2,3,4,4a,5,8,9,10,10a-decahydrophenanthrene which is reacted with hydrogen peroxide in the presence of formic acid as per Example 1F to give the title compound.

EXAMPLE 20

2,3-trans-4a,9a-trans-perhydro-6(and 7)dimethylaminofluorene-2,3,4a,7(and 6),9a-pentol.

To a solution of 34 g (0.20 mole) of 1,1a,4,4a,9a-tetrahydrofluorene in 250 ml CHCl₃ is added dropwise at 10°–15°C a solution of 0.25 mole of 85% m-chloroperbenzoic acid in 500 ml CHCl₃. After stirring several hours, the mixture is filtered cold and the filtrate washed with dilute base. The dried organics are taken to dryness and the crude epoxide mixed with a benzene solution containing excess dimethylamine in a pressure vessel. After 16 hours at 100°–120°, the bomb is cooled and the contents taken to dryness on a rotary evaporator, leaving crude 2(and 3)dimethylamino-3(and 2)-hydroxy-1,2,3,4,4a,9a-hexahydrofluorene, which is subjected to Birch reduction as per Example 1E to provide 2(and 3)dimethylamino-3(and 2)hydroxy-1,2,3,4,5,8,4a,9a-octahydrofluorene, which is reacted with hydrogen peroxide in the presence of formic acid as per Example 1F to form the title compound.

EXAMPLE 21

4-Dimethylaminomethyl-2,3,4b,6,7,8a-hexahydroxy-perhydrofluorene

A solution of 0.1 mole of fluorene-4-carboxylic acid in 25 ml abs. ethanol is added to 500 ml of liquid NH₃ and the sol'n is treated with 0.6 mole of lithium cut in small pieces. After reduction in NH₃ is complete, 250 ml of ether is added; NH₃ is evaporated and just sufficient HCl added to acidify the mixture. The cold layers are quickly separated and the organics dried and added to a suspension of 15 g of LAH in 500 ml of ether. After 3 hrs of reflux, the mixture is decomposed with saturated K₂CO₃ solution and the organic filtrates freed of solvent to give the oily 1,4,4a,9a-tetrahydrofluorenyl-4-carbinol.

The crude alcohol is dissolved in CHCl₃ and treated at 0°–5°C with a few drops of pyridine then excess phosphorus tribromide. After several hours in the cold, the mixture is poured onto ice and the organic layer washed with dilute K₂CO₃ and dried. Solvent removal leaves the desired bromide.

The above halide is taken up in benzene and added to a benzene solution of excess dimethylamine. After several hours, it is heated on the steam bath to complete the alkylation. Solvent removal leaves the oily 4-dimethylaminomethyl-1,1a,4,4a-tetrahydrofluorene which is subjected to the Birch reduction procedure as per Example 1E and the hydroxylation as per Example 1F to yield 4-dimethylaminoethyl-2,3,4b,6,7,8a-hexahydroxy-perhydro-fluorene.

EXAMPLE 22

2,3-trans-4a,9a-trans-Dodecahydro-8-(diethylaminomethyl)-8-methylfluorene-2,3,4a,9a-tetrol A. 1-Diethylaminomethyl-1-methyl-1,2,3,4,4a,9a-hexahydrofluorene To 10.8 g (0.05 mole) of 1-methyl-1,2,3,4,4a,9a-hexahydrofluorene-1-carboxylic acid (Ind. J. Chem. 5 459 (1967)) is added 50 ml (XS) thionyl chloride and the solution heated on the steam bath for 2 hrs. Excess reagent is removed on the water aspirator and then benzene added and removed twice. The residual acid chloride is taken up in 50 ml of benzene and added with cooling and stirring to a solution of 10 g (XS) of diethylamine in 50 ml of benzene. Stirring is continued for several hours, the precipitated salt filtered off and the filtrate washed with water. Concentration of the dried organic filtrate leaves 12.2 g crude amide. The amide is dissolved in 50 ml of dioxane and added dropwise to a suspension of 5 g of lithium aluminum hydride in 100 ml of ether. After several hours at reflux, the mixture is decomposed with saturated $K_2CO_3$ and filtered. Concentration of the filtrates leave 10.5 g of the title compound.

B. 1-Diethylaminoethyl-1-methyl-1,2,3,4,5,8,4a,9a-octahydrofluorene

The 1-diethylaminomethyl-1-methyl-1,2,3,4,1a,4a-hexahydrofluorene of part B is then subjected to a Birch reduction as per Example 1, part E, to form the title compound.

C. 2,3-trans-4a,9a-trans-Dodecahydro-8-(diethylaminomethyl)-8-methylfluorene-2,3,4a,9a-tetrol The diene compound prepared in part B is then reacted with hydrogen peroxide in the presence of formic acid as per Example 1, part F, to form the title compound.

EXAMPLE 23

2,3-trans-4a,9a-trans-Dodecahydro-9-(dimethylaminoethyl)-9-methylfluorene-2,3,4a,9a-tetrol A solution of 43.2 g (0.20 mole) of 1-methyl-1,2,3,4,4a,9a-hexahydrofluorene-1-carboxylic acid in 250 ml of dioxane is added dropwise to a suspension of 25 g of lithium aluminum hydride in 1 l. of ether and the mixture stirred under reflux for 3 hrs. After decomposition with saturated potassium carbonate solution, the mixture is filtered, and solvent removed from the filtrate leaving a quantitative yield of 1-methyl-1,2,3,4,4a,9a-hexahydrofluorenyl-1-carbinol.

The above alcohol is taken up in 200 ml of $CHCl_3$, treated with a few ml of pyridine, cooled in an ice bath and stirred while 20 g of phosphorus tribromide is added dropwise. After stirring for several hours cold, the mixture is poured onto ice water, the layers separated, and the organic layer dried over magnesium sulfate and freed of solvent, leaving the desired, 1-methyl-1,2,3,4,4a,9a-hexahydro-1-fluorenylmethyl bromide.

The above bromide is dissolved in 500 ml of solvent, consisting of 20% t-butanol and 80% N-methyl-2-pyrrolidine, and treated with 25 g of KCN. The stirred mixture is heated on the steam bath for 6 hrs. cooled and poured into water. The product is extracted into ether and the aqueous portion reextracted several times. The combined organic extracts are washed with water, dried and taken to dryness, ultimately on the oil pump, leaving about 30 g of desired 1-methyl-1,2,3,4,4a,9a-hexahydro-1-fluorenylacetonitrile as an oil.

The above nitrile is dissolved in 100 ml of ether and added to a suspension of 15 g of LAH in 500 ml of ether dropwise over 15 min. After 3 hrs at reflux, the mixture is decomposed with sat'd $K_2CO_3$ and filtered. Solvent removal from the filtrate leaves 28 g of oily 2'-[1-methyl-1,2,3,4,4a,9a-tetrahydro-1-fluorenyl]-ethylamine.

The above amine is treated with 25 ml of 37% formalin in the cold, followed by 35 ml of 88% formic acid with swirling. The solution is then heated on the steam bath overnight, then taken to dryness in vacuum. The residue is dissolved in water, rendered strongly basic with 50% caustic and extracted with ether. Removal of solvent from the dried extracts leaves about 30 g of oil N,N-dimethyl-2'-[1-methyl-1,2,3,4,1a,4a-hexahydrofluorenyl]-ethylamine.

This is then subjected to a Birch reduction as per Example 1E to give N,N-dimethyl-[1-methyl-1,2,3,4,5,8,4a,9a-octahydro-1-fluorenyl]-2'-ethylamine; which is reacted with hydrogen peroxide in the presence of formic acid as per Example 1F to form the title compound.

EXAMPLE 24

2,3-trans-4a,9a-trans-Dodecahydro-4b-(ethylmethylaminomethyl)-fluorene-2,3,4a,9a-tetrol A. 4a-Ethylmethylaminomethyl-1,2,3,4,4a,9a-hexahydrofluorene To 10.8 g of (0.05 mole) of 1,2,3,4,4a,9a-hexahydrofluorene-4a-carboxylic acid (JOC 34 1899 (1969)) is added 50 ml (XS) thionyl chloride and the solution heated on the steam bath for 2 hrs. Excess reagent is removed on the water aspirator and then benzene added and removed twice. The residual acid chloride is taken up in 50 ml of benzene and added with cooling and stirring to a solution of 10 g (XS) of ethylmethylamine in 50 ml of benzene. Stirring is continued for several hours, the precipitated salt filtered off and the filtrate washed with water. Concentration of the dried organic filtrate leaves 12.2 g crude amide. The amide is dissolved in 50 ml of dioxane and added dropwise to a suspension of 5 g of lithium aluminum hydride in 100 ml of ether. After several hours at reflux, the mixture is decomposed with saturated $K_2CO_3$ and filtered. Concentration of the filtrates leave 10.5 g of the title compound.

B. 4a-Ethylmethylaminomethyl-1,2,3,4,5,8,4a,9a-octahydrofluorene

The 1-ethylmethylaminomethyl-1,2,3,4,4a,9a-hexahydrofluorene of part A is then subjected to a Birch reduction as per Example 1, part E, to form the title compound.

C. 2,3-trans-4a,9a-trans-Dodecahydro-4b-(ethylmethylaminomethyl)-fluorene-2,3,4a,9a-tetrol The diene compound prepared in part B is then reacted with hydrogen peroxide in the presence of formic acid as per Example 1, part F, to form the title tetrol compound.

EXAMPLE 25

2,3-trans-4a,9a-trans-Dodecahydro-4b-(dimethylaminoethyl)-fluorene-2,3,4a,9a-tetrol A solution of 43.2 g (0.20 mole) of 1,2,3,4,4a,9a-hexahydrofluorene-4a-carboxylic acid in 250 ml of dioxane is added dropwise to a suspension of 25 g of lithium aluminum hydride in 1 l. of ether and the mixture stirred under reflux for 3 hrs. After decomposition with saturated potassium carbonate solution, the mixture is filtered, and solvent removed from the filtrate leaving a quantitative yield of 1,2,3,4,4a,9a-hexahydrofluorenyl-4a-carbinol.

The above alcohol is taken up in 200 ml of $CHCl_3$, treated with a few ml of pyridine, cooled in an ice bath and stirred while 20 g of phosphorus tribromide is added dropwise. After stirring for several hours cold, the mixture is poured onto ice water, the layers separated, and the organic layer dried over magnesium sulfate and freed of solvent, leaving the desired, 1,2,3,4,4a,9a-hexahydro-4a-fluorenylmethyl bromide.

The above bromide is dissolved in 500 ml of solvent, consisting of 20% t-butanol and 80% N-methyl-2-pyrrolidine, and treated with 25 g of KCN. The stirred mixture is heated on the steam bath for 6 hrs, cooled and poured into water. The product is extracted into ether and the aqueous portion reextracted several times. The combined organic extracts are washed with water, dried and taken to dryness, ultimately on the oil pump, leaving about 30 g of desired 1,2,3,4,4a,9a-hexahydro-4-fluorenylacetonitrile as an oil.

The above nitrile is dissolved in 100 ml of ether and added to a suspension of 15 g of LAH in 500 ml of ether dropwise over 15 min. After 3 hrs at reflux, the mixture is decomposed with sat'd $K_2CO_3$ and filtered. Solvent removal from the filtrate leaves 28 g of oily 2'-[1,2,3,4,4a,9a-tetrahydro-4-fluorenyl]-ethylamine.

The above amine is treated with 25 ml of 37% formalin in the cold, followed by 35 ml of 88% formic acid with swirling. The solution is then heated on the steam bath overnight, then taken to dryness in vacuum. The residue is dissolved in water, rendered strongly basic with 50% caustic and extracted with ether. Removal of solvent from the dried extracts leaves about 30 g of oil N,N-dimethyl-2'-[1,2,3,4,4a,9a-hexahydro-4a-fluorenyl]-ethylamine.

This is then subjected to a Birch reduction as per Example 1E to give N,N-dimethyl-[1,2,3,4,5,8,4a,9a-octahydro-4a-fluorenyl]-2'-ethylamine; which is reacted with hydrogen peroxide in the presence of formic acid as per Example 1F to form the title compound.

EXAMPLE 26

2,3-trans-4a,9a-trans-Dodecahydro-4b-(dimethylamino)fluorene-2,3,4a,9a-tetrol

A. 4a-Dimethylamino-1,2,3,4,5,8,4a,9a-octahydrofluorene

4a-Dimethylamino-1,2,3,4,1a,4a-hexahydrofluorene (JOC 28, 1112 (1963)) is subjected to a Birch reduction as per Example 1, part E, to form the title compound.

B. 2,3-trans-4a,9a-trans-Dodecahydro-4b-(dimethylamino)fluorene-2,3,4a,9a-tetrol The diene compound prepared in part A is then reacted with hydrogen peroxide in the presence of formic acid as per Example 1, part F, to form the title tetrol compound.

What is claimed is:
1. A compound of the structure

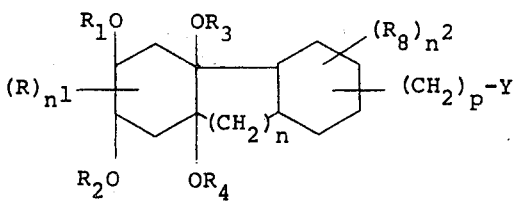

wherein $n$ is 1 or 2; $n^1$ is 0, 1 or 2; $n^2$ is 0, 1, 2, or 3; $p$ is an integer of from 0 to 10; $R_1$, $R_2$, $R_3$ and $R_4$ are the same or different and are selected from the group consisting of hydrogen, an acyl radical having less than 12 carbon atoms selected from the group consisting of lower alkanoyl, lower alkenoyl, monocyclic aroyl, monocyclic aryl-lower alkanoyl, cycloalkanoyl, cycloalkenoyl, cycloalkyl-lower alkanoyl and cycloalkenyl-lower alkanoyl, lower alkyl, trifluoromethyl, monohalo-lower alkyl, lower alkoxy-carbonyl, amido and (lower alkoxy) alkylene wherein the alkylene group has 2 to 5 carbon atoms; R is selected from the group consisting of lower alkyl, lower alkoxy, and cycloalkyl; $R_8$ is selected from the group consisting of hydrogen, lower alkyl, cycloalkyl, di-lower alkylamino-lower alkyl, hydroxy and $R_9O(CH_2)_q$— wherein $R_9$ can be any of the $R_1$ to $R_4$ groups set forth above and $q$ is an integer of from 1 to 10; and Y is

wherein $R_5$ and $R_6$ may be the same or different and are selected from the group consisting of hydrogen, lower alkyl, lower alkoxy, halo-lower alkyl, monocyclic cycloalkyl, monocyclic cycloalkyl-lower alkyl, hydroxy-lower alkyl, monocyclic aryl or monocyclic aryl-lower alkyl; or

can be taken together to form a 5-, 6- or 7-membered nitrogen heterocyclic radical containing not more than one hetero atom in addition to the nitrogen atom, wherein said additional hetero atom may be oxygen, nitrogen, or sulfur; wherein the term cycloalkyl refers to cycloalkyl groups having 3 to 6 carbon atoms and wherein the term aryl refers to phenyl or phenyl substituted with lower alkyl, halogen, nitro, or lower alkoxy; stereoisomers thereof, acid salts thereof, quaternary salts thereof and N-oxides thereof.

2. A compound in accordance with claim 1 wherein each of $R_1$, $R_2$, $R_3$ and $R_4$ is hydrogen.

3. A compound in accordance with claim 1 wherein one, two, three or each of $R_1$, $R_2$, $R_3$ and $R_4$ is acyl and the remainder hydrogen.

4. A compound in accordance with claim 1 wherein all four OR groups are axial and $R_1O$ and $R_2O$ are in trans configuration and $OR_3$ and $OR_4$ are in trans configuration.

5. A compound in accordance with claim 1 wherein $R_1O$ and $R_2O$ are in trans configuration and $OR_3$ and $OR_4$ are in trans configuration and $R_3O$ and $R_4O$ are diaxial and $R_1O$ and $R_2O$ are diequatorial.

6. A compound in accordance with claim 1 wherein $R_1O$ and $R_2O$ are in cis configuration and $OR_3$ and $OR_4$ are in trans configuration and one of $R_1O$ and $R_2O$ is equatorial and the other axial and $OR_3$ and $OR_4$ are diaxial.

7. A compound in accordance with claim 1 wherein $R_1O$ and $R_2O$ are in trans configuration and $OR_3$ and $OR_4$ are in cis configuration and $R_1O$ and $R_2O$ are diequatorial or diaxial and one of $OR_3$ and $OR_4$ is equatorial and the other axial.

8. A compound in accordance with claim 1 wherein $n$ is 1.

9. A compound in accordance with claim 1 wherein n is 2.

10. A compound in accordance with claim 1 wherein $R_8$ is hydroxyl or $HO(CH_2)_q$ and n is 1 or 2.

11. A compound in accordance with claim 1 wherein the [-X-Y] —$(CH_2)_p$—Y group and $R_8$ group are attached to the same carbon atom.

12. A compound in accordance with claim 1 having the structure

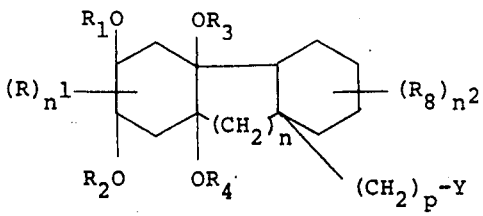

13. The compound in accordance with claim 1 having the name 2,3-trans-4a,9a-trans-dodecahydro-6-(1-pyrrolidinyl)-fluorene-2,3,4a,9a-tetrol, tetraacetate ester.

14. The compound in accordance with claim 1 having the name 2,3-trans-4a,9a-trans-dodecahydro-7-(hydroxymethyl)-8-(piperidinomethyl)fluorene-2,3,4a,9a-tetrol, pentaacetate ester.

15. The compound in accordance with claim 1 having the name 2,3-trans-4a,9a-trans-dodecahydro-8-(hydroxymethyl)-7-(piperidinomethyl)fluorene-2,3,4a,9a-tetrol, pentaacetate ester.

16. The compound in accordance with claim 1 having the name 2,3-trans-4a,9a-trans-dodecahydro-6-(1-pyrrolidinyl)-fluorene-2,3,4a,9a-tetrol.

17. The compound in accordance with claim 1 having the name 2,3-trans-4a,9a-trans-dodecahydro-7-(1-pyrrolidinyl)-fluorene-2,3,4a,9a-tetrol.

18. The compound in accordance with claim 1 having the name 2,3-trans-4a,9a-trans-dodecahydro-7-(1-pyrrolidinyl)-fluorene-2,3,4a, 9a-tetrol, tetraacetate ester.

* * * * *

UNITED STATES PATENT AND TRADEMARK OFFICE
CERTIFICATE OF CORRECTION

PATENT NO. : 3,984,419
DATED : October 5, 1976
INVENTOR(S) : Frederic P. Hauck et al.

It is certified that error appears in the above-identified patent and that said Letters Patent are hereby corrected as shown below:

Abstract page, "$R^1\overset{O}{\underset{\|}{C}}$," should read -- ($R^1\overset{O}{\underset{\|}{C}}$), --

Column 16, line 18, "XI" should read -- IX --.

Column 38, structure LXXII should read:

Column 38, structure LXXIV should read:

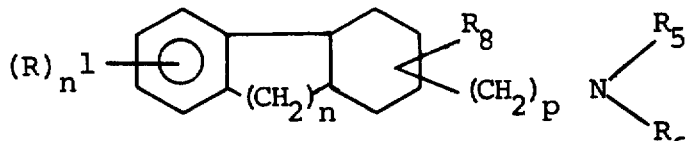

Column 41, the title of Example 1-A. should read: (lines 1&2)
  10,10A-Dihydro-4H-fluorene[1,2-c]furan-1,3-(3aH,10bH)-dione Column 41, line 8, "186.6°" should read -- 186.5° --.
Column 44, line 2, "than" should read -- then --.
Column 47, line 3, "H,8.043;" should read -- H,8.03; --.
Column 48, line 21, "2,3,4a,9A" should read -- 2,3,4a,9a --.
Column 57, line 6, please omit "[-X-Y]"

Signed and Sealed this

Twenty-second Day of March 1977

[SEAL]

Attest:

RUTH C. MASON
Attesting Officer

C. MARSHALL DANN
Commissioner of Patents and Trademarks